(12) United States Patent
Zhang et al.

(10) Patent No.: US 10,478,477 B2
(45) Date of Patent: Nov. 19, 2019

(54) METHOD FOR PROPHYLAXIS OR TREATMENT OF ERBB1 POSITIVE CANCERS USING A VARIANT PEPTIDASE D WITH REDUCED ACTIVITY

(71) Applicant: Health Research, Inc., Buffalo, NY (US)

(72) Inventors: Yuesheng Zhang, Orchard Park, NY (US); Lu Yang, Buffalo, NY (US); Yun Li, Orchard Park, NY (US); Arup Bhattacharya, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 0 days.

(21) Appl. No.: 15/504,560

(22) PCT Filed: Aug. 20, 2015

(86) PCT No.: PCT/US2015/046000
§ 371 (c)(1),
(2) Date: Feb. 16, 2017

(87) PCT Pub. No.: WO2016/028956
PCT Pub. Date: Feb. 25, 2016

(65) Prior Publication Data
US 2017/0232078 A1    Aug. 17, 2017

Related U.S. Application Data

(60) Provisional application No. 62/039,497, filed on Aug. 20, 2014.

(51) Int. Cl.
*A61K 38/48* (2006.01)
*C12N 9/48* (2006.01)
*A61K 45/06* (2006.01)
*A61P 35/00* (2006.01)

(52) U.S. Cl.
CPC .......... *A61K 38/4813* (2013.01); *A61K 38/48* (2013.01); *A61K 45/06* (2013.01); *A61P 35/00* (2018.01); *C12N 9/485* (2013.01); *C12Y 304/13009* (2013.01); *C07K 2319/55* (2013.01)

(58) Field of Classification Search
None
See application file for complete search history.

(56) References Cited

U.S. PATENT DOCUMENTS

| 6,812,339 B1 | 11/2004 | Venter et al. |
| 2002/0103133 A1 | 8/2002 | Copeland et al. |
| 2006/0134088 A1 | 6/2006 | Ammannati et al. |
| 2006/0177448 A1 | 8/2006 | Carey et al. |
| 2010/0173978 A1 | 7/2010 | D'Alessio et al. |
| 2013/0165389 A1 | 6/2013 | Schellenberger et al. |

FOREIGN PATENT DOCUMENTS

| WO | 2004/104595 A2 | 12/2004 | | |
| WO | 2004104595 A2 | 12/2004 | | |
| WO | WO 2004/104595 | * 12/2004 | ............. | G01N 33/68 |
| WO | WO 2005/053713 | * 6/2005 | ........... | A61K 31/727 |
| WO | 2007110767 A2 | 10/2007 | | |

OTHER PUBLICATIONS

MyBioSource, Inc. Human PEPD ELISA kit (2013).*
Perez-Torres et al, Epidermal Growth Factor Receptor (EGFR) Antibody Down-regulates Mutant Receptors and Inhibits Tumors Expressing EGFR Mutations. J Biol Chem vol. 281, No. 52, pp. 40183-40192, Dec. 29, 2006.*
Yang et al, Prolidase Directly Binds and Activates Epidermal Growth Factor Receptor and Stimulates Downstream Signaling.J Biol Chem vol. 288, No. 4, pp. 2365-2375, Jan. 25, 2013.*
Fan et al, Antibody-induced Epidermal Growth Factor Receptor Dimerization Mediates Inhibitiono f Autocrine Proliferation oAf 431 Squamous Carcinoma Cells. J Biol Chem vol. 269, No. 44, Issue of Nov. 4, pp. 27595-27602, 1994.*
Howe et al, Targeting the HER/EGFR/ErbB Family to Prevent Breast Cancer. Cancer Prev Res; 4(8) Aug. 2011 pp. 1149-1157.*
Wu et al., A Meta-Analysis of Genome-Wide Association Studies for Adiponectin Levels in East Asians Identities a Novel Locus Near WDR11-FGFR2: Homo sapiens peptidase D (PEPD), Transcript Variant 1, mRNA, NCBI Reference Sequence: MN_000285.3, Hum. Mol. Genet., vol. 23, No. 4, pp. 1108-1119 May 17, 2014.
Lima et al., Activation of blood coagulation in cancer: implications for tumour progression, Bioscience Reports, vol. 33, pp. 701-710. Jul. 26, 2013.
Yang et a., Inhibition of ERBB2-overexpressing Tumors by Recombinant Human Prolidaes and Its Enzymatically Inactive Mutant, Ebiomedicine, vol. 2, No. 5, pp. 396-405. May 1, 2015.
Azemar et al., Regression of Cutaneous Tumor Lesions in Patients Intratumorally Injected with a Recominant Single-chain Antibody-toxin Targeted to ErbB2/HER2, Breast Cancer Research and Treatment, vol. 82, No. 3, pp. 155-164 Dec. 1, 2003.
Kitchener et al., Prolidase function in proline metabolism and its medical and biotechnological applications, Journal of Applied Microbiology, vol. 113, No. 2 Jul. 31, 2012.

(Continued)

*Primary Examiner* — Sheridan Swope
(74) *Attorney, Agent, or Firm* — Hodgson Russ LLP

(57) ABSTRACT

Provided are compositions and methods for prophylaxis and/or therapy of ErbB1-positive cancer. The compositions include pharmaceutical preparations that contain isolated or recombinant or modified peptidase D (PEPD) proteins. The methods include prophylaxis and/or therapy of ErbB1-positive cancer by administering a PEPD to an individual who has or is at risk for developing ErbB1-positive cancer.

5 Claims, 10 Drawing Sheets
Specification includes a Sequence Listing.

(56) References Cited

OTHER PUBLICATIONS

Yang et al., Prolidase Directly Binds and Activates Epidermal Growth Factor Receptor and Stimulates Downstream Signaling, Journal Biological Chemistry, vol. 288, No. 4, pp. 2365-2375. Dec. 4, 2012.

Yang, L., et al., Identification of prolidase as a high affinity ligand of the ErbB2 receptor and its regulation of ErbB2 signaling and cell growth, Cell Death and Disease, May 8, 2014, vol. 5, No. 5, e1211, 9 pages.

* cited by examiner

A

B

C

SEQUENCE LISTING

```
<160> NUMBER OF SEQ ID NOS: 13

<210> SEQ ID NO 1
<211> LENGTH: 493
<212> TYPE: PRT
<213> ORGANISM: Human

<400> SEQUENCE: 1

Met Ala Ala Ala Thr Gly Pro Ser Phe Trp Leu Gly Asn Glu Thr Leu
1               5                   10                  15

Lys Val Pro Leu Ala Leu Phe Ala Leu Asn Arg Gln Arg Leu Cys Glu
            20                  25                  30

Arg Leu Arg Lys Asn Pro Ala Val Gln Ala Gly Ser Ile Val Val Leu
        35                  40                  45

Gln Gly Gly Glu Glu Thr Gln Arg Tyr Cys Thr Asp Thr Gly Val Leu
    50                  55                  60

Phe Leu Gln Glu Ser Phe Phe His Trp Ala Phe Gly Val Thr Glu Pro
65                  70                  75                  80

Gly Cys Tyr Gly Val Ile Asp Val Asp Thr Gly Lys Ser Thr Leu Phe
                85                  90                  95

Val Pro Arg Leu Pro Ala Ser His Ala Thr Trp Met Gly Lys Ile His
            100                 105                 110

Ser Lys Glu His Phe Lys Glu Lys Tyr Ala Val Asp Asp Val Gln Tyr
        115                 120                 125

Val Asp Glu Ile Ala Ser Val Leu Thr Ser Gln Lys Pro Ser Val Leu
    130                 135                 140

Leu Thr Leu Arg Gly Val Asn Thr Asp Ser Gly Ser Val Cys Arg Glu
145                 150                 155                 160

Ala Ser Phe Asp Gly Ile Ser Lys Phe Glu Val Asn Asn Thr Ile Leu
                165                 170                 175

His Pro Glu Ile Val Glu Ser Arg Val Phe Lys Thr Asp Met Glu Leu
            180                 185                 190

Glu Val Leu Arg Tyr Thr Asn Lys Ile Ser Ser Glu Ala His Arg Glu
        195                 200                 205

Val Met Lys Ala Val Lys Val Gly Met Lys Glu Tyr Gly Leu Glu Ser
    210                 215                 220

Leu Phe Glu His Tyr Cys Tyr Ser Arg Gly Gly Met Arg His Ser Ser
225                 230                 235                 240

Tyr Thr Cys Ile Cys Gly Ser Gly Glu Asn Ser Ala Val Leu His Tyr
                245                 250                 255

Gly His Ala Gly Ala Pro Asn Asp Arg Thr Ile Gln Asn Gly Asp Met
            260                 265                 270

Cys Leu Phe Asp Met Gly Gly Glu Tyr Tyr Ser Val Ala Ser Asp Ile
        275                 280                 285

Thr Cys Ser Phe Pro Arg Asn Gly Lys Phe Thr Ala Asp Gln Lys Ala
    290                 295                 300
```

-continued

Val Tyr Glu Ala Val Leu Leu Ser Ser Arg Ala Val Met Gly Ala Met
305                 310                 315                 320

Lys Pro Gly Asp Trp Trp Pro Asp Ile Asp Arg Leu Ala Asp Arg Ile
                325                 330                 335

His Leu Glu Glu Leu Ala His Met Gly Ile Leu Ser Gly Ser Val Asp
            340                 345                 350

Ala Met Val Gln Ala His Leu Gly Ala Val Phe Met Pro His Gly Leu
        355                 360                 365

Gly His Phe Leu Gly Ile Asp Val His Asp Val Gly Gly Tyr Pro Glu
    370                 375                 380

Gly Val Glu Arg Ile Asp Glu Pro Gly Leu Arg Ser Leu Arg Thr Ala
385                 390                 395                 400

Arg His Leu Gln Pro Gly Met Val Leu Thr Val Glu Pro Gly Ile Tyr
                405                 410                 415

Phe Ile Asp His Leu Leu Asp Glu Ala Leu Ala Asp Pro Ala Arg Ala
            420                 425                 430

Ser Phe Leu Asn Arg Glu Val Leu Gln Arg Phe Arg Gly Phe Gly Gly
        435                 440                 445

Val Arg Ile Glu Glu Asp Val Val Ile Asp Ser Gly Ile Glu Leu
    450                 455                 460

Leu Thr Cys Val Pro Arg Thr Val Glu Glu Ile Glu Ala Cys Met Ala
465                 470                 475                 480

Gly Cys Asp Lys Ala Phe Thr Pro Phe Ser Gly Pro Lys
                485                 490

<210> SEQ ID NO 2
<211> LENGTH: 21
<212> TYPE: DNA
<213> ORGANISM: artificial sequence
<220> FEATURE:
<223> OTHER INFORMATION: primer

<400> SEQUENCE: 2
aatacgactc actatagggc g                                       21

<210> SEQ ID NO 3
<211> LENGTH: 17
<212> TYPE: DNA
<213> ORGANISM: artificial sequence
<220> FEATURE:
<223> OTHER INFORMATION: primer

<400> SEQUENCE: 3
cttggggcca gagaagg                                            17

<210> SEQ ID NO 4
<211> LENGTH: 36
<212> TYPE: DNA
<213> ORGANISM: artificial sequence
<220> FEATURE:
<223> OTHER INFORMATION: primer

<400> SEQUENCE: 4
ataagaatgc ggccgcagct gagattcccc tccatt                       36

<210> SEQ ID NO 5
<211> LENGTH: 36
<212> TYPE: DNA
<213> ORGANISM: artificial sequence
<220> FEATURE:
<223> OTHER INFORMATION: primer

```
<400> SEQUENCE: 5
atagtttagc ggccgccttg atgccagcag aagtca                              36

<210> SEQ ID NO 6
<211> LENGTH: 21
<212> TYPE: DNA
<213> ORGANISM: artificial sequence
<220> FEATURE:
<223> OTHER INFORMATION: primer

<400> SEQUENCE: 6
caaatgggcg gtaggcgtgt a                                              21

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
attggtgggc aggtaggtga gttc                                           24

<210> SEQ ID NO 8
<211> LENGTH: 23
<212> TYPE: DNA
<213> ORGANISM: artificial sequence
<220> FEATURE:
<223> OTHER INFORMATION: primer

<400> SEQUENCE: 8
ctgtttgccg tgccaccctg agt                                            23

<210> SEQ ID NO 9
<211> LENGTH: 24
<212> TYPE: DNA
<213> ORGANISM: artificial sequence
<220> FEATURE:
<223> OTHER INFORMATION: primer

<400> SEQUENCE: 9
cttctgctgc cgtcgcttga tgag                                           24

<210> SEQ ID NO 10
<211> LENGTH: 19
<212> TYPE: DNA
<213> ORGANISM: artificial sequence
<220> FEATURE:
<223> OTHER INFORMATION: primer

<400> SEQUENCE: 10
ccagggctgc ttttaactc                                                 19

<210> SEQ ID NO 11
<211> LENGTH: 18
<212> TYPE: DNA
<213> ORGANISM: artificial sequence
<220> FEATURE:
<223> OTHER INFORMATION: primer

<400> SEQUENCE: 11 gctccccct gcaaatga                                                   18

<210> SEQ ID NO 12
```

```
<211> LENGTH: 20
<212> TYPE: DNA
<213> ORGANISM: artificial sequence
<220> FEATURE:
<223> OTHER INFORMATION: primer

<400> SEQUENCE: 12
tggaatctac tggcgtcttc                                            20

<210> SEQ ID NO 13
<211> LENGTH: 20
<212> TYPE: DNA
<213> ORGANISM: artificial sequence
<220> FEATURE:
<223> OTHER INFORMATION: primer

<400> SEQUENCE: 13
caccaccttc ttgatgtcct                                            20
```

METHOD FOR PROPHYLAXIS OR TREATMENT OF ERBB1 POSITIVE CANCERS USING A VARIANT PEPTIDASE D WITH REDUCED ACTIVITY

CROSS-REFERENCE TO RELATED APPLICATIONS

This application claims priority to U.S. Provisional Application No. 62/039,497, filed on Aug. 20, 2014, the disclosure of which is incorporated herein by reference.

BACKGROUND OF THE DISCLOSURE

Epidermal growth factor receptor (EGFR), also known as ErbB1 or HER-1, is a cell surface receptor that plays a major role in a variety of cellular responses. It is a member of four closely related receptor tyrosine kinases: ErbB1, ErbB2 (HER-2), ErbB3 (HER-3), ErbB4 (HER-4). Ligand binding to the extracellular domain of these receptors leads to homo- or heterodimerization, followed by receptor tyrosine phosphorylation and phosphorylation/activation of many signaling proteins involved in an array of cellular events. Key signaling pathways downstream of ErbB receptors include the PI3K/AKT/mTOR pathway, the Ras/Raf/ERK pathway, and the JAK/STAT pathway. ErbB activation results in an increase in DNA synthesis, cell growth, cell proliferation, cell differentiation, and cell migration, which perhaps is most clearly demonstrated in cancer cells. Indeed, the ErbB receptors have become major drug targets in cancer therapy. Overexpression or activating mutations in the kinase domain of the ErbB receptors are known to be associated with a variety of cancers.

ErbB1 overexpression or activating mutations in its kinase domain occur in many cancers, including, but not limited to, brain cancer, breast cancer, colon cancer, lung cancer, and head and neck cancer. Several ErbB1-targeting drugs are on market, including penitumumab, cetuximab, gefitinib, erlotinib and afatinib. Penitumumab (IgG2 isotype) and cetuximab (IgG1 isotype) are monoclonal antibodies, whereas gefitinib, erlotinib and afatinib are low-molecular weight tyrosine kinase inhibitors. However, many patients are either intrinsically insensitive to these agents or develop acquired resistance. Therefore, there is an ongoing and unmet need to develop novel therapeutic approaches to targeting ErbB1 in cancer. The present disclosure meets this need.

BRIEF SUMMARY OF THE DISCLOSURE

The present disclosure provides compositions and methods useful for prophylaxis and/or therapy of ErbB1-positive cancers. The compositions and methods relate in part to the discovery that prolidase or peptidase D (referred to herein as PEPD) is a ligand of the ErbB1 receptor. However, in contrast to a previous report (Yang, et al., *Prolidase directly binds and activates epidermal growth factor receptor and stimulates downstream signaling*, J Biol Chem. 2013 Jan. 25; 288(4):2365-75) which described stimulation of ErbB and cancer cell proliferation via PEPD binding to ErbB1, the present disclosure demonstrates that PEPD can be used to inhibit the growth of ErbB1+ cancer cells. In particular, the present disclosure provides a demonstration of rapid PEPD-ErbB1 binding-induced inhibition of the growth of cancer cells that overexpress ErbB1, whereas growth of cancer cells that express low or moderate levels of ErbB1 is initially stimulated (24 hour treatment), but is then inhibited (after 24 hours); see, e.g., FIGS. 5, 6B). Further, this disclosure is believed to be the first description of any ErbB1 ligand that cross-links two ErbB1 monomers. By "cross-link" it is meant that two ErbB1 monomers are simultaneously bound by a single PEPD dimer, but does not mean the ErB1 dimers are covalently bound to one another.

Prolidase, also known as mentioned above as peptidase D (PEPD), Xaa-Pro dipeptidase or proline dipeptidase, or imidodipeptidase, is a protease which hydrolyzes dipeptides with proline or hydroxyproline at the carboxy terminus. PEPD is a ubiquitously expressed cytosolic protein and exists as a homodimer (monomeric molecular weight of human PEPD: 54 kD; 493 amino acids as shown in SEQ ID NO: 1 below, which provides the amino acid sequence of human prolidase). In embodiments, the PEPD that is used for the compositions and methods of the instant disclosure is a mammalian PEPD. In one embodiment, the PEPD is human PEPD. In embodiments, the PEPD can be enzymatically active or have reduced or have no detectable enzymatic activity.

The compositions for use in methods disclosed herein comprise pharmaceutical preparations which contain an isolated and/or purified PEPD or recombinant and/or modified PEPD, and can further comprise additional agents, such as an anticoagulant. In embodiments the PEPD is modified. In embodiments, the PEPD is a component of a fusion protein. In embodiments, the fusion protein comprises the PEPD and an amino acid sequence useful for purification of recombinantly produced PEPD.

The methods comprise administering to an individual in need of prophylaxis and/or therapy of an ErbB1-positive cancer a composition comprising a PEPD of this disclosure, and can further comprise administering to the individual an anticoagulant. Also provided are methods for identifying individuals in need of treatment with PEPD formulations, and methods for generating a treatment protocol for such individuals.

In embodiments the disclosure further provides products comprising pharmaceutical preparations which contain an isolated and/or purified PEPD or recombinant PEPD, and which can also contain printed material describing use of the preparations for prophylaxis and/or therapy of ErbB1-positive cancers as an indication. In embodiments, the products also contain an anticoagulant. In non-limiting embodiments, the ErbB1-positive cancers comprise brain cancer, breast cancer, colon cancer, head and neck cancer, and lung cancer. In embodiments, ErbB1-positive cancer cells are cancer cells which overexpress ErbB1 relative to non-cancer cells, or carry a higher copy number of the ERBB1 gene relative to non-cancer cells. In embodiments, ErbB1-positive cancer cells express ErbB1 with an activating mutation.

C. All samples were then subjected to pull-down by protein A sepharose beads and western blotting for rhPEPD, Fc and/or ErbB1-Fc. BSA was used to rule out nonspecific binding of rhPEPD. EGF was used to confirm specific binding to rhPEPD to ErbB1. (B) Binding of hPEPD to ErbB1, measured by ELISA. Each value is mean±SD (n=3). The Kd value was estimated by non-linear regression (GraphPad Prism 6 software). (C) Murine myeloid 32D cells do not express any ErbBs. 32D cells stably expressing human ErbB1 were generated by gene transfection and selection. 32D/ErbB1 cells were treated with vehicle, rhPEPD or rhPEPD$^{G278D}$ (5 nM), and then treated with cross-linking agent bis(sulfosuccinimidyl)suberate (BS3; 2 mM, 30 min); cell lysates were analyzed by western blotting for ErbB1.

Figure 2:
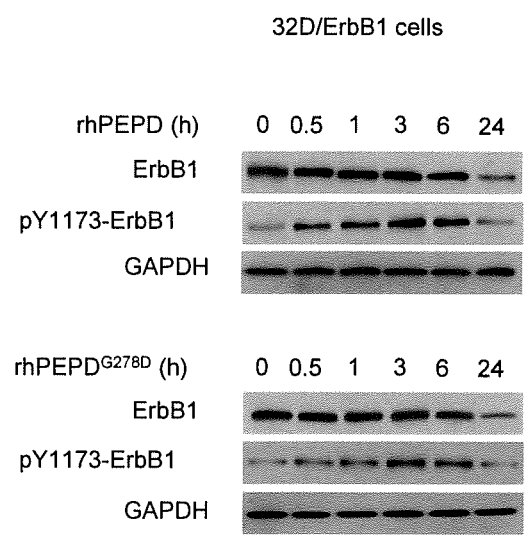

FIG. 2. Data showing rhPEPD or rhPEPD$^{G278D}$ causes ErbB1 phosphorylation and later ErbB1 depletion. 32D/ErbB1 cells were treated with rhPEPD or rhPEPD$^{G278D}$ (5 nM) for different time, followed by western blotting of ErbB1 and ErbB1 phosphorylation. Glyceraldehyde 3-phosphate dehydrogenase (GAPDH) is a loading control.

Figure 3:
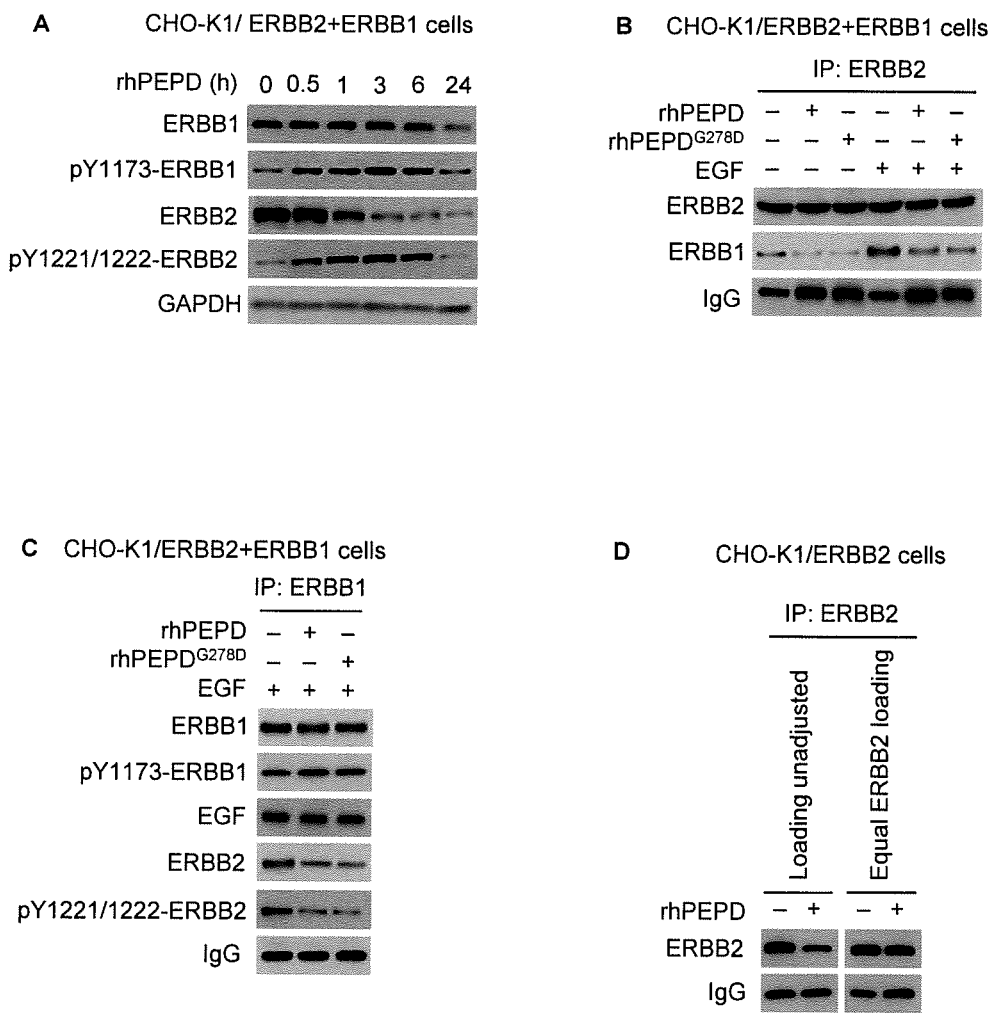

FIG. 3. Data showing that rhPEPD and rhPEPD$^{G278D}$ modulate both ErbB1 and ErbB2 and disrupt ErbB1-ErbB2 heterodimerization. (A) CHO-K1 cells stably overexpressing human ErbB2 were transfected with human ErbB1 for 24 h and then treated with rhPEPD (5 nM), followed by western blotting of ErbB1, phosphorylated ErbB1, ErbB2, and phosphorylated ErbB2. GAPDH is a loading control. (B, C) CHO-K1 cells stably overexpressing human ErbB2 were transfected with human ErbB1 for 24 h and then treated with solvent, rhPEPD or rhPEPD$^{G278D}$ (5 nM) for 1 h, with or without pretreatment with EGF (20 nM, 15 min). Cell lysates were immunoprecipitated using an ErbB2 antibody or an ErbB1 antibody, followed by immunoblotting. For the immunoblots shown in B, sample loading was adjusted to contain an equal amount of ErbB2. (D) Immunoblotting with and without ErbB2 loading adjustment. CHO-K1 cells stably overexpressing ErbB2 were treated with rhPEPD at 5 nM for 1 h. Cell lysates were incubated with an ErbB2 antibody, and the immunocomplexes were pulled down with protein G-agarose, followed by immunoblotting for ErbB2. Sample loading was either adjusted to contain an equal amount of ErbB2 or not adjusted.

Figure 4:
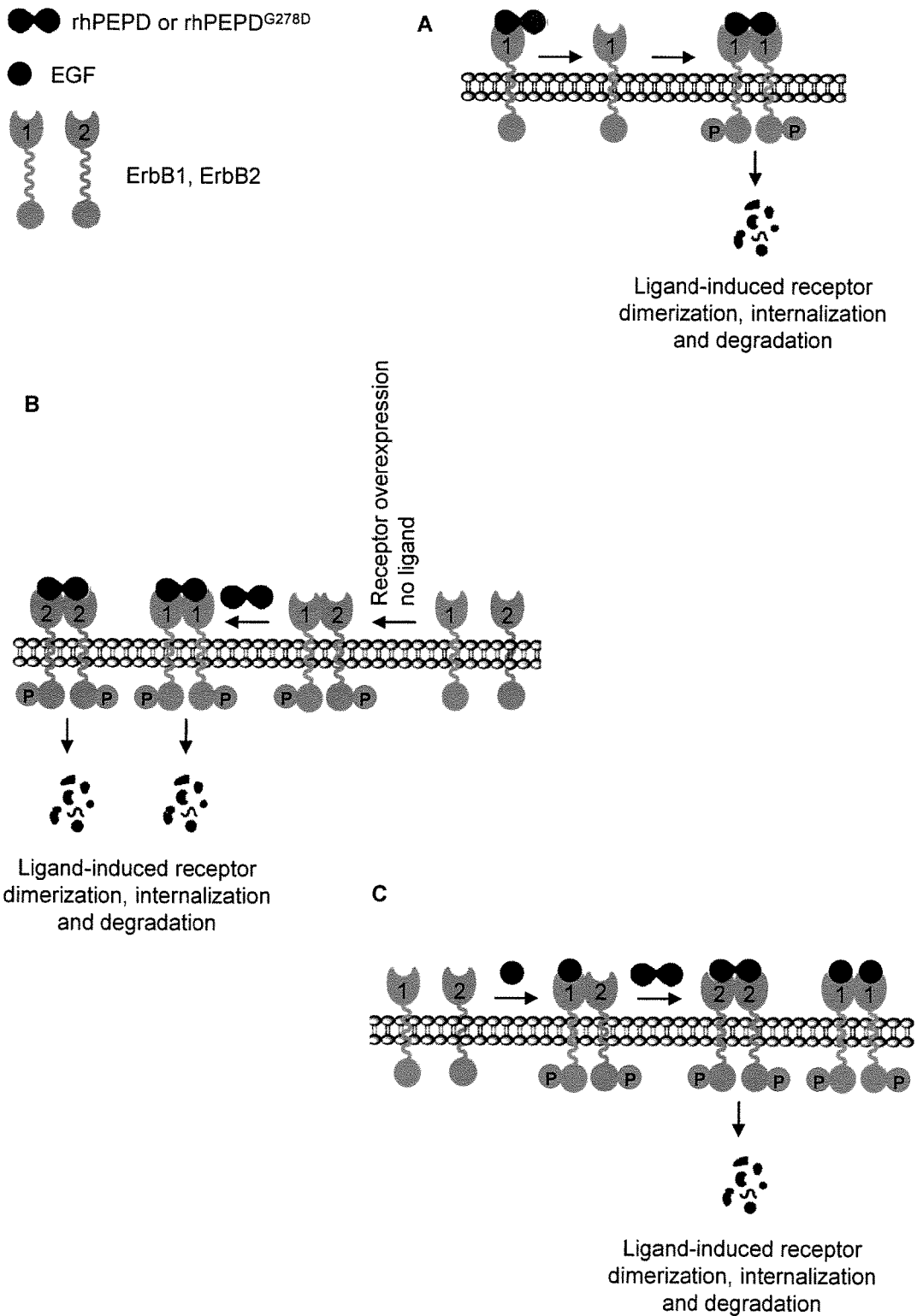

FIG. 4. Graphic showing paradigm of ErbB1 and ErbB2 modulation by rhPEPD and rhPEPD$^{G278D}$. (A) Homodemeric rhPEPD or rhPEPD$^{G278D}$ binds and cross-links two ErbB1 monomers, which leads to ErbB1 phosphorylation and depletion, the latter of which results from internalization and degradation. (B) Overexpression of ErbB and/or ErbB2 leads to heterdimerization and receptor phosphorylation in the absence of a ligand. rhPEPD or rhPEPD$^{G278D}$ disrupts ErbB1-ErbB2 heterodimerization by cross-linking two ErbB1 monomers and two ErbB2 monomers, leading to receptor depletion due to internalization and degradation. Notably, despite binding to both ErbB1 and ErbB2, neither rhPEPD nor rhPEPD$^{G278D}$ cross-links ErbB1 and ErbB2; (C) EGF induces ErbB1-ErbB2 heterodimerization, but both rhPEPD and rhPEPD$^{G278D}$ disrupt such dimerization by cross-linking two ErbB2 monomers and causing ErbB2 depletion via internalization and degradation.

Figure 5:
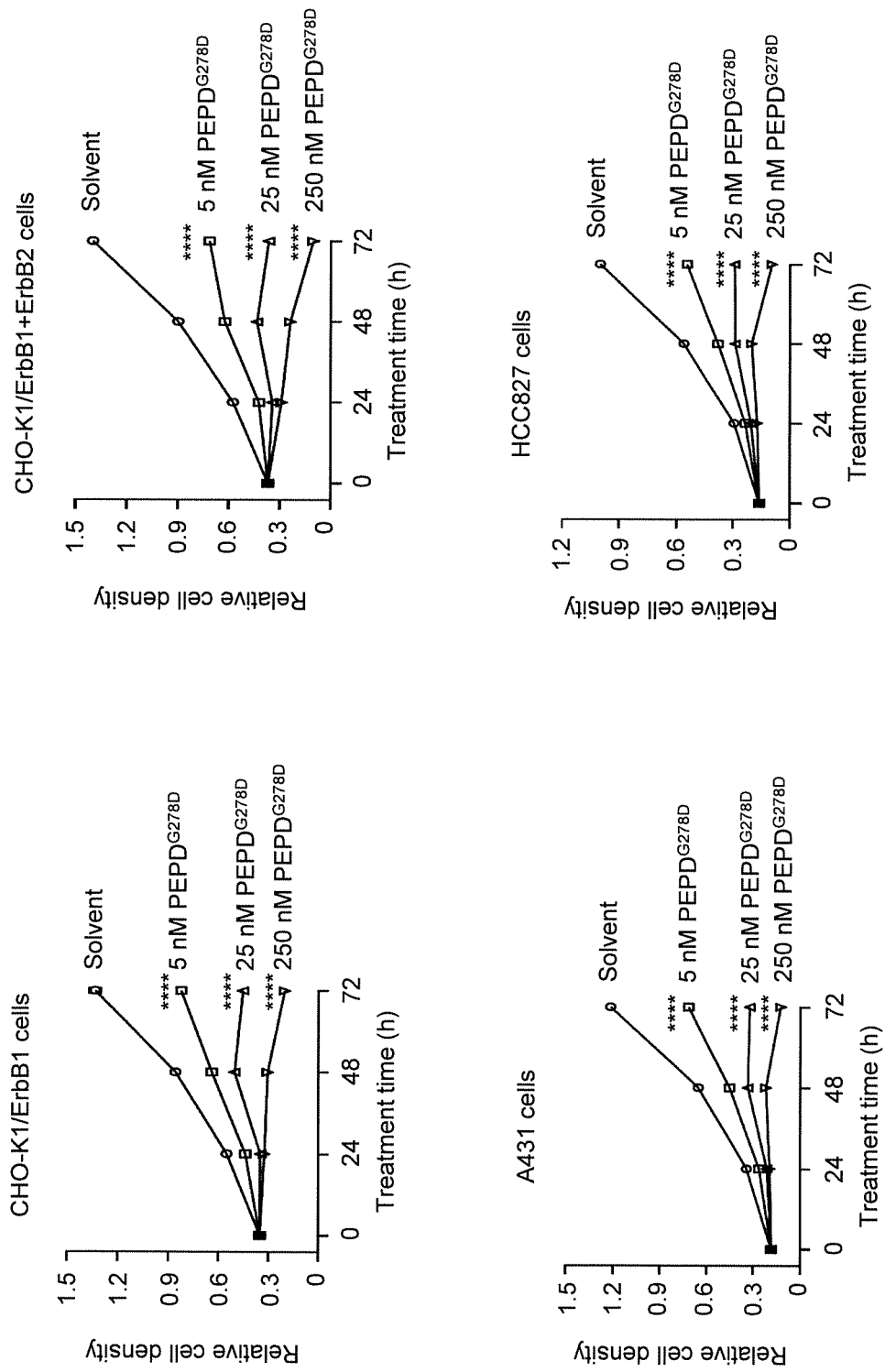

FIG. 5. Data showing rhPEPD$^{G278D}$ inhibition of proliferation of cancer cells that overexpress ErbB1 or ErbB1 with an activating mutation. The cells lines evaluated include CHO-K1 cells that stably overexpress human ErbB1 (CHO-K1 ErbB1 cells), CHO-K1 cells that stably overexpress both human ErbB and human ErbB2 (CHO-K1 ErbB1/ErbB2 cells), human epidermoid carcinoma A431 cells that overexpress human ErbB1, and human lung adenocarcinoma HCC827 cells that express an activating mutation in the ErbB1 tyrosine kinase domain (E746-A750 deletion). Cells were grown in 96-well plates overnight and then treated with solvent or rhPEPD$^{G278D}$ for 24, 48 or 72 h, followed by measurement of cell proliferation by MTT assay. Each value is mean±SD (n=3). The data at 72 h time point were analyzed by one-way ANOVA, followed by Tukey multiple comparisons test, **** P<0.0001.

Figure 6:
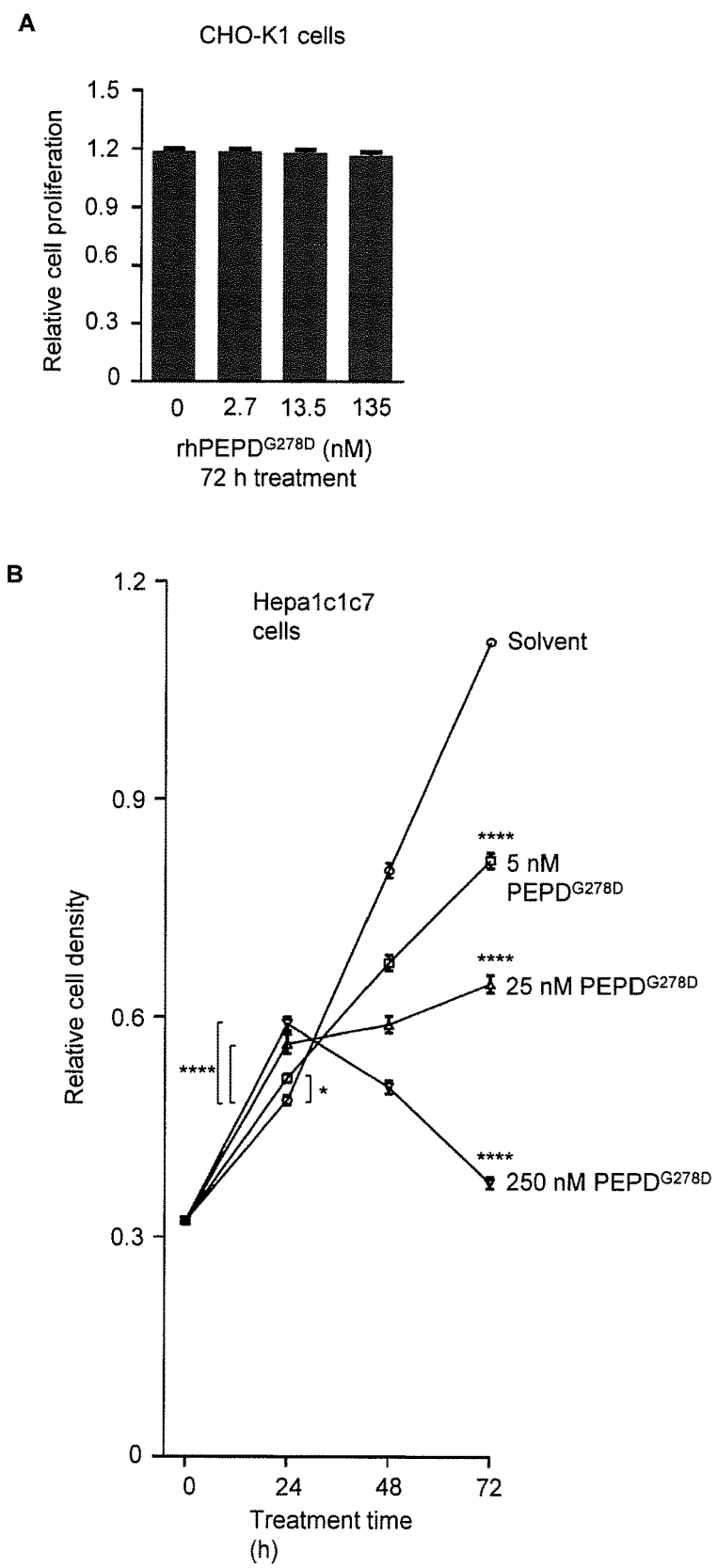

FIG. 6. Data showing no effect of rhPEPD$^{G278D}$ on the proliferation of cells that do not express ErbB1, whereas rhPEPD$^{G278D}$ causes biphasic effect on cell proliferation (initial modest stimulation, followed by marked inhibition) in cells with moderate expression of ErbB1. (A) CHO-K1 cells (no ErbB1) were grown in 96-well plates overnight and then treated with solvent or rhPEPD$^{G278D}$ for 72 h, followed by measurement of cell proliferation by MTT assay. Each value is mean±SD (n=3). (B) Murine hepatoma Hepa1c1c7 cells (moderate level of ErbB1) were grown in 96-well plates overnight and then treated with solvent or rhPEPD$^{G278D}$ for 24, 48 or 72 h, followed by measurement of cell proliferation by MTT assay. Each value is mean±SD (n=3). The data at 24 h and 72 h time points were analyzed by one-way ANOVA, followed by Tukey multiple comparisons test, * P<0.05, **** P<0.0001.

Figure 7:
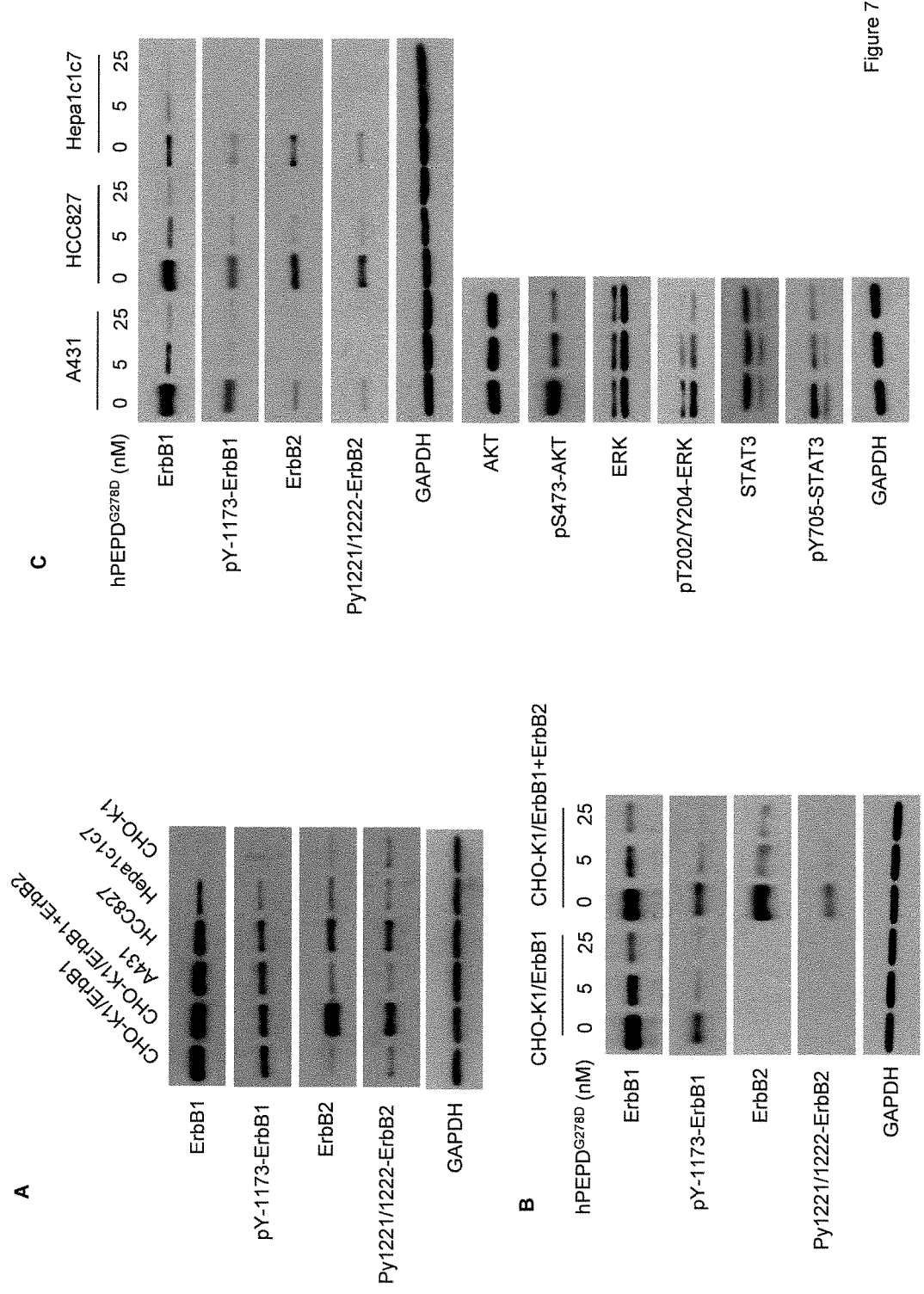

FIG. 7. Data showing that rhPEPD$^{G278D}$ silences ErbB1 and ErbB2 (receptor depletion and corresponding decrease in receptor tyrosine phosphorylation) in various cancer cell lines. (A) Expression and tyrosine phosphorylation of ErbB1 and ErbB2 in CHO-K1/ErbB1 cells, CHO-K1/ErbB1+ErbB2 cells, A431 cells, HCC827 cells, Hepa1c1c7 cells, and CHO-K1 cells. Cell lysates were analyzed by western blotting. Representative phosphorylation sites were measured. (B, C) Cells were treated with solvent or hPEPD$^{G278D}$ at 5 or 25 nM for 48 h, followed by preparation of cell lysates and western blot analysis of ErbB1, ErbB2 and their phosphorylation. For A431 cells, AKT, p-AKT, ERK, p-ERK, STAT3 and p-STAT3 were also measured.

Figure 8:
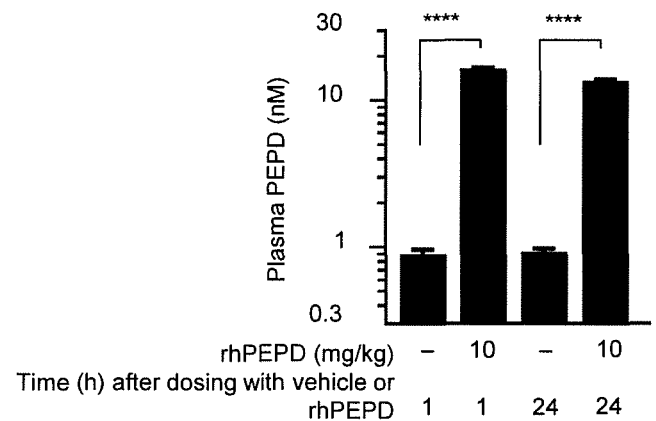
Figure 8:
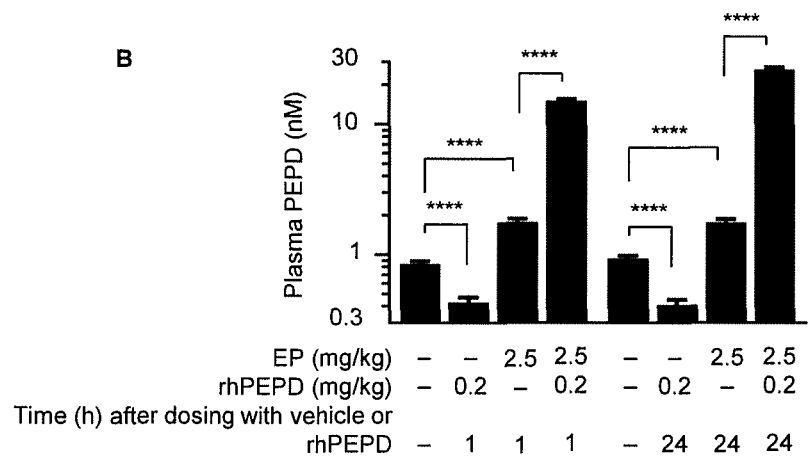
Figure 8:
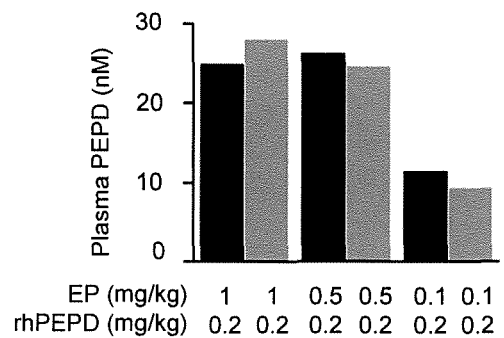

FIG. 8. Data showing that enoxaparin (EP), a clinically used anticoagulant, elevates plasma concentration of PEPD. EP is a clinically used low molecular weight heparin (LMWH). C57BL/6 mice (male, 7-8 weeks of age) were used in the experiments. Plasma levels of endogenous mouse PEPD or total PEPD (endogenous mouse PEPD plus rhPEPD) was measured by ELISA. EP and rhPEPD were given to mice in PBS. (A) Plasma concentrations of endogenous mouse PEPD and total PEPD in mice at 1 or 24 h after receiving a single i.p. dose of vehicle or rhPEPD. Error bars are SD (n=3). Data were log transformed and analyzed by two-way ANOVA, followed by Tukey multiple comparisons test, ** P<0.0001. (B) Mice were either untreated or treated with EP i.p. once daily for 4 days; 1 h after the last EP dose, the EP-treated mice were given an i.p. dose of vehicle or rhPEPD, followed by measurement of plasma levels of mouse PEPD and total PEPD at 1 or 24 h post final dosing. Error bars are SD (n=3). Data were log transformed and analyzed by two-way ANOVA, followed by Tukey multiple comparisons test, ** P<0.0001. (C) EP at different doses was administered to mice i.p. once daily; 1 h after the fourth EP dose, the mice were injected i.p. with vehicle or rhPEPD. Plasma concentrations of total PEPD were measured at 1 and 24 h after giving the vehicle or rhPEPD. Each bar represents 1 sample (2 mice per group).

Figure 9:
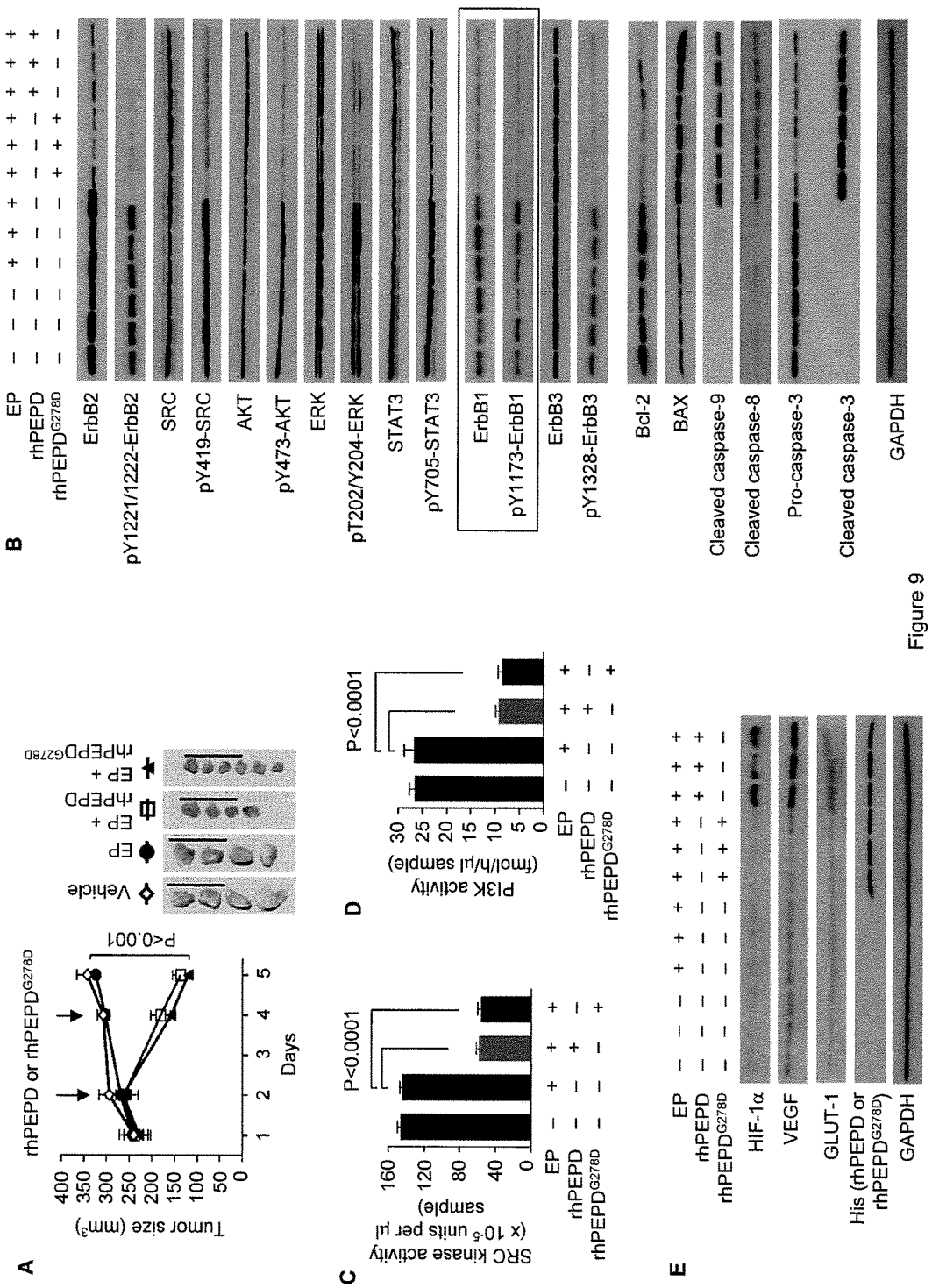

FIG. 9. Data showing inhibition of tumor growth and molecular changes in tumor tissues after treatment with rhPEPD or rhPEPD$^{G278D}$. Human breast cancer BT-474 cells constitutively overexpress ErbB2 but also express a low level of ErbB1 and ErbB3. BT-474 cells were inoculated to the mammary fat pads of female athymic mice. Mice were treated after tumor size reached approximately 230 mm$^3$. (A) Sizes of orthotopic BT-474 tumors upon treatment with vehicle, EP, EP plus rhPEPD or EP plus rhPEPD$^{G278D}$. EP was administered to the mice by intraperitoneal injection (i.p.) at 0.5 mg/kg daily, starting 4 days before rhPEPD or rhPEPD$^{G278D}$ rhPEPD and rhPEPD$^{G278D}$ were administered to the mice at 2 mg/kg i.p. twice, separated by 2 days. The mice were killed 24 h after the final doses. Error bars are SEM (n=4-6). Scale bars: 3 cm. (B) Immunoblots comparing major cell signaling changes in tumor specimens obtained 24 h after the final dose of each treatment as indicated in A. Each sample represents one tumor. (C, D) SRC kinase activity and PI3K activity in tumor specimens obtained 24 h after the final dose of each treatment as indicated in A. Error bars are SD (n=3). (E) Immunoblots comparing HIF-1α signaling changes in tumor specimens obtained 24 h after the final dose of each treatment as indicated in A. Each sample represents one tumor. The above results show that rhPEPD$^{G278D}$ is superior to rhPEPD for tumor inhibition. Data in (A, C, D) were analyzed by two-way ANOVA.

Figure 10:
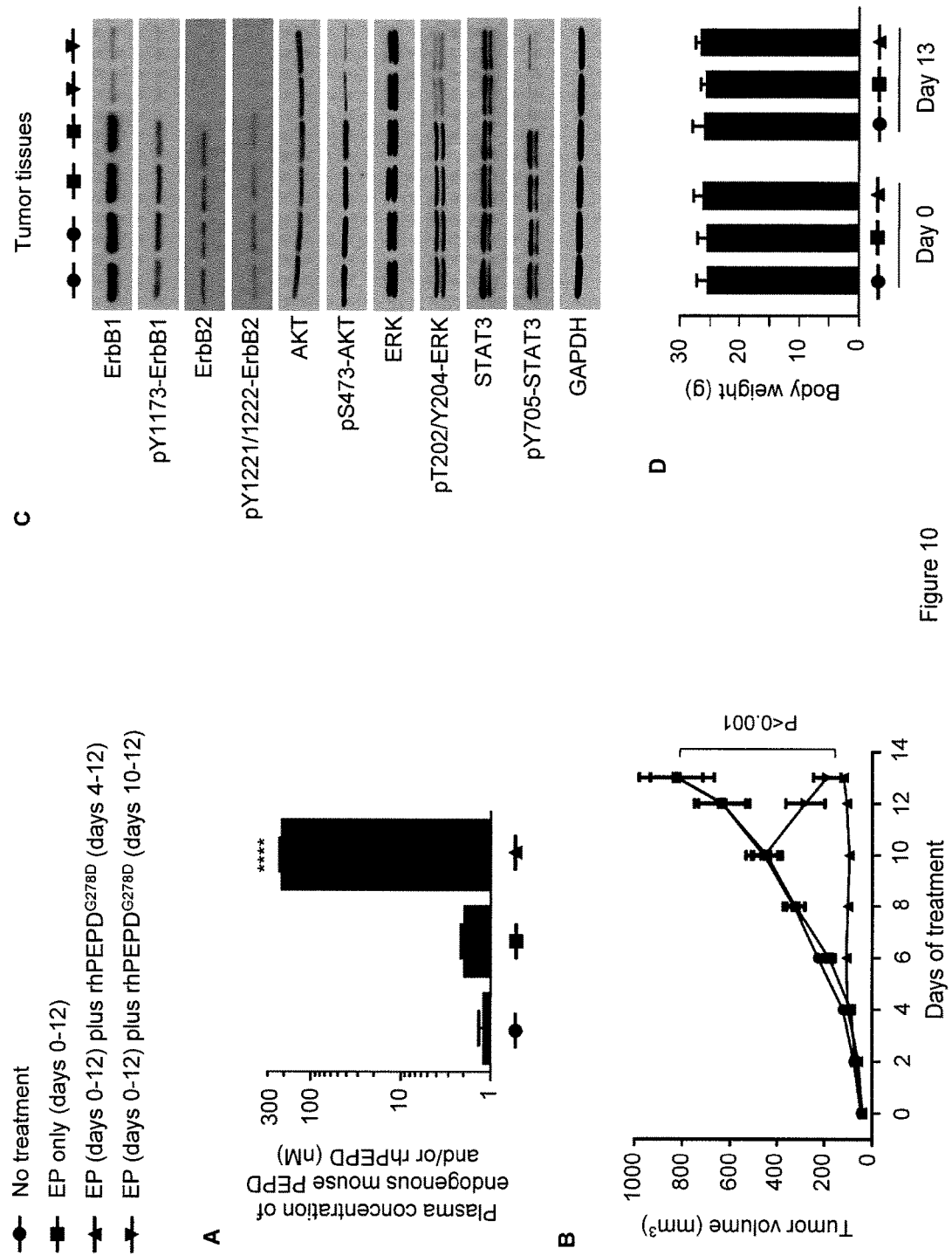

FIG. 10. Data showing tumor growth inhibition and inhibition of ErbB1 signaling in tumor tissues from mice treated with rhPEPD$^{G278}$ as well as high plasma concentration of rhPEPD$^{G278D}$. Male athymic mice (5-6 weeks of age) bearing subcutaneous A431 tumors were untreated, treated with EP, or EP plus rhPEPD$^{G278D}$. EP (0.5 mg/kg) was administered to the mice daily i.p. for a total of 13 doses; rhPEPD$^{G278D}$ (4 mg/kg) was administered to the mice i.p. every other day for a total of 2 doses (started after 11 doses of EP) or 5 doses (started after 5 doses of EP). When EP and rhPEPD$^{G278D}$ were given to the same mice on the same day, rhPEPD$^{G278D}$ was given 1 h after EP. Blood samples as well as tumors were obtained from the mice at 24 h after the last treatment or at the same time from the untreated mice. Plasma concentrations of endogenous mouse PEPD and/or rhPEPD$^{G278D}$ were determined by ELISA. Error bars indicate SD (n=3). The data were analyzed by one-way ANOVA, ** P<0.0001, compared with the vehicle control. (A) Plasma concentrations of endogenous mouse PEPD and/or rhPEPD$^{G278D}$ were determined by ELISA. Error bars indicate SD (n=3). The data were analyzed by one-way ANOVA, ** P<0.0001, compared with the no treatment control. (B) Tumor size in control mice and mice treated with EP or EP plus rhPEPD$^{G278D}$. Each value is mean±SEM (n=4-10). The data were analyzed by one-way ANOVA. (C) Changes of signaling molecules in tumors from control mice or mice treated with EP or EP plus rhPEPD$^{G278D}$. Each lane represents one tumor. (A) Mouse body weight at the beginning and end of treatment (mean±SD).

DETAILED DESCRIPTION OF THE DISCLOSURE

Unless specified to the contrary, it is intended that every maximum numerical limitation given throughout this description includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The present disclosure is based at least in part on our discoveries that PEPD or its enzymatically-inactive mutant binds to ErbB1, inhibits the growth of cancer cells that are driven by ErbB1, or both ErbB1 and ErbB2 in vitro, inhibits the growth of ErbB1-driven cancer in mouse models, and causes the depletion of ErbB1 (and ErbB2) and inhibition of oncogenic signaling in cancer cells and cancer tissues. In particular, with respect to ErbB1, it has been shown that human PEPD binds ErbB1 and stimulates the proliferation of ErbB1 expressing cells in vitro (Yang et al., Journal of Biological Chemistry, 288, 2365-2375, 2013). However, in contrast to that observation, and as described above, it is demonstrated in the present disclosure that treatment of cancer cells with PEPD for more than 24 h causes significant and time-dependent inhibition of cell growth, which is associated with ErbB1 depletion and other changes. PEPD and its enzymatically inactive mutant (PEPD$^{G278D}$) directly bind to the ectodomain of ErbB1 and cross-link two ErbB1 monomers, leading to ErbB1 internalization and degradation, although ErbB1 phosphorylation is increased transiently. Our data also show the PEPD and its mutant disrupt ErbB heterodimerization with ErbB2. This suggests that PEPD or PEPD mutants may be useful against ErbB1-driven cancers showing de nova or acquired resistance to current ErbB1-targeted therapies. The resistance mechanisms include but not limited to ErbB2 overexpression and second-site mutations (Yonesaka et al., Science Translational Medicine 3, 99ra86, 2011; Lin and Bivona, Chemotherapy Research and Practice 2012, article ID 817297, 2012). PEPD and PEPD$^{G278D}$ may overcome such resistance by targeting both ErbB1 and ErbB2 and by employing their novel targeting mechanism, i.e., cross-linking two monomers of ErbB1 or ErbB2. Notably, no existing anti-ErbB1 agents are known to cross-link ErbB1 monomers.

As described above, by "cross-link" and "cross-linking" it is meant that two ErbB1 monomers (or two ErbB2 monomers) are simultaneously bound by a single PEPD dimer, but does not mean that such dimers are covalently bound to one another. A representative and non-limiting illustration of such cross-linking is shown in FIG. 4A for ErbB1 cross-linked as a homodimer, and for ErB1 and ErbB2 homodimers as shown in FIGS. 4B and 4C. We have not found evidence of PEPD cross-linked ErbB1/ErbB2 heterodimers.

The mRNA sequence and amino acid sequence of ErbB are provided in NCBI reference sequence: NM_005228.3 and NP_005219.2. While variants in ErbB1 are known in the art, it is expected that the present method will function with any ErbB1 variant, provided that the ErbB1 variant has an extracellular domain. The extracellular domain is known in the art. The disclosure also includes compositions and methods for prophylaxis and therapy of cancer cells expressing variants of these sequences, such as those which have mutated or truncated C-termini, but which retain the extracellular domain (ECD); the ECD being well known in the art.

The present disclosure reveals a fundamentally different and new function of PEPD. PEPD has been known as a cytosolic dipeptidase, but an enzymatically-inactive PEPD mutant (PEPD$^{G278D}$) is as effective as PEPD itself in modulating ErbB1. PEPD$^{G278D}$ may be more efficacious than PEPD for tumor inhibition because, as demonstrated in this disclosure, the enzymatic function of rhPEPD stimulates HIF-1α signaling (FIG. 9E) which may attenuates PEPD antitumor activity. PEPD$^{G278D}$ is also more attractive that PEPD itself in that the former may not interfere with the enzymatic function of endogenous PEPD in normal cells. Further, although a previous report indicated that PEPD is a relatively low affinity ErbB1 ligand (Kd=5.3 µM), as measured by ELISA (Yang et al., Journal of Biological Chemistry 288, 2365-2375, 2013), the present disclosure demonstrates a much higher binding affinity (Kd=392.6 nM; see FIG. 1B).

The inhibitory impact of PEPD and PEPD$^{G278D}$ on ErbB1 stands in stark contrast to the well-known stimulatory impact of other ErbB ligands on their receptors. Given the high cost of current ErbB1-targeting agents, e.g., cetuximab which costs up to $30,000 for eight weeks of treatment per patient, PEPD has the advantage that it can be mass produced recombinantly as further described below at a relatively low cost, and is therefore expected in certain embodiments to be a significant and less expensive alternative to cetuximab and other currently available anti-ErbB1 agents.

Any PEPD is expected to be suitable for use in the compositions and methods of the present disclosure. In embodiments, the PEPD is a PEPD produced by a prokaryote or a eukaryote. In embodiments, the PEPD is prokaryotic in origin. In non-limiting embodiments, the PEPD is produced by *Pseudoalteromonas haloplanktis* (i.e., a PEPD comprising the amino acid sequence under GenBank no. AAA99824.1), or *Pyrococcus furiosus* (i.e., a PEPD comprising the amino acid sequence under GenBank no. WP_011011876.1). A number of eukaryotic PEPD amino acid sequences are also known in the art, including a number of mammalian PEPD amino acid sequences. In embodiments, the PEPD has the sequence of a rodent PEPD, i.e., a mouse or rat, or a non-human primate PEPD, such as chimpanzee or a Rhesus macaque. The amino acid sequence of mouse prolidase is provided under GenBank accession no. NP_032846.2; rat prolidase is provided under NP_001009641.1; Rhesus macaque prolidase is provided under AFJ71215.1; chimpanzee prolidase is provided under NP_001267459.1. The amino acid sequence of human prolidase (PEPD) in SEQ ID NO:1 is known in the art. SEQ ID NO:1 and the cDNA sequence encoding it is accessible via GenBank accession no. J04605.1; the amino acid sequence is also provided under GenBank accession number AAA60064. In one illustrative but not limiting embodiment, enzymatically active human PEPD has the sequence of SEQ ID NO:1:

```
                                        (SEQ ID NO: 1)
MAAATGPSFWLGNETLKVPLALFALNRQRLCERLRKNPAVQAGSIVVLQG

GEETQRYCTDTGVLFLQESFFHWAFGVTEPGCYGVIDVDTGKSTLFVPRL

PASHATWMGKIHSKEHFKEKYAVDDVQYVDEIASVLTSQKPSVLLTLRGV

NTDSGSVCREASFDGISKFEVNNTILHPEIVESRVFKTDMELEVLRYTNK

ISSEAHREVMKAVKVGMKEYGLESLFEHYCYSRGGMRHSSYTCICGSGEN

SAVLHYGHAGAPNDRTIQNGDMCLFDM*G*EYYSVASDITCSFPRNGKF

TADQKAVYEAVLLSSRAVMGAMKPGDWWPDIDRLADRIHLEELAHMGILS

GSVDAMVQAHLGAVFMPHGLGHFLGIDVHDVGGYPEGVERIDEPGLRSLR

TARHLQPGMVLTVEPGIYFIDHLLDEALADPARASFLNREVLQRFRGFGG

VRIEEDVVVIDSGIELLTCVPRTVEEIEACMAGCDKAFTPFSGPK
```

In SEQ ID NO: 1, the G at position 278 is shaded, bolded and italicized and represents the location of a G278D mutation which renders the PEPD enzymatically inactive. In embodiments, the mutation is a change of glycine at position 278 to an amino acid other than aspartic acid.

All of the amino acid and polynucleotide sequences provided under the GenBank accession numbers referenced in this disclosure are incorporated herein by reference as those sequences were available through GenBank on the date of filing of this application. This disclosure also includes all polynucleotides encoding PEPD and all variants of it that are described herein or which would otherwise be known to the skilled artisan given the benefit of the present disclosure.

Rodent (mouse and rat) PEPD amino acid sequences are more than 86% similar to the human sequence, while non-human primate PPED amino acid sequences, such as the Rhesus macaque, is over 95% similar to the human PEPD amino acid sequence. In embodiments, the PEPD comprises or consists of a human PEPD amino acid sequence. In embodiments, the PEPD used in the compositions and/or methods of the present disclosure is at between at least 85.0% and 99.9%, inclusive, and including all numerals to the first decimal place there between, similar to the sequence of SEQ ID NO: 1. In an embodiment, the PEPD comprises an amino acid sequence that is at least 95% similar to the sequence of SEQ ID NO: 1.

In various embodiments, the present disclosure includes use of compositions comprising wild type PEPD (e.g., PEPD of SEQ ID NO: 1), or modified PEPD, or a combination thereof. In general, modifications to PEPD suitable for use with the present invention can be determined by those skilled in the art using ordinary techniques, given the benefit of the present description. In embodiments, modified PEPD comprises modifications of SEQ ID NO: 1. The disclosure includes all modifications of SEQ ID NO: 1 so long as the PEPD retains the capability to bind to and cause depletion of ErbB1 from the cell surface. In embodiments, modified PEPD retains the capability to form a homodimer. In embodiments, contacting an ErbB1-positive cell with a modified (or wild type) PEPD of this disclosure is followed by ErbB1 binding and endocytosis of ErbB1, resulting in ErbB1 depletion. Modified PEPD that maintains some or all of these functional attributes may comprise amino acid insertions, deletions and substitutions. For example, the disclosure includes PEPD which has been modified by conservative amino acid substitutions that are based generally on relative similarity of R— group substituents. Non-limiting examples of such substitutions include gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, a PEPD that comprises any single conservative amino acid substitution, or any combination of conservative amino acid substitutions, are included in the disclosure provided they can at least retain the capability to bind to ErbB1, with subsequent depletion of ErbB1 from the cell surface. It will be apparent to those skilled in the art how to determine whether or not any particular modified PEPD can bind to ErbB1. In embodiments, the modified PEPD can bind the ErbB extracellular domain with an estimated Kd value of 392.6 nM, as determined using an ELISA assay.

Wild type PEPD is enzymatically active. Modified PEPD is a PEPD that comprises a change in SEQ ID NO: 1 and can be enzymatically active or enzymatically inactive. In this regard, it is known in the art that defects in the iminodipeptidase activity of PEPD is associated with a Prolidase Deficiency, which is a very rare autosomal recessive disease associated with collagen metabolism and affects connective tissues. Thus it is known that the enzymatic activity of PEPD is important. However, in embodiments, enzymatically inactive PEPD is used in the compositions and methods of this disclosure. Enzymatically inactive PEPD is considered to be a PEPD that exhibits less hydrolysis of a substrate dipeptide that has proline or hydroxyproline at its carboxy terminus than the amount of such hydrolysis exhibited by a reference protein which comprises or consists of the sequence of SEQ ID NO: 1. In embodiments, enzymatically inactive PEPD can have enzymatic activity between 0.0%, −99.9%, inclusive, and including all digits there between to the first decimal point, less dipeptide hydrolysis activity as compared to a reference PEPD. In one embodiment, an enzymatically inactive PEPD has no more than 0.6% dipeptide hydrolysis activity of a reference PEPD. In one embodiment, the reference PEPD comprises or consists of the sequence of SEQ ID NO: 1. One unit of prolidase activity may be defined as the amount of enzyme that releases 1 µmol of proline/h under standard assay conditions. In one embodiment, an enzymatically inactive PEPD has no detectable PEPD dipeptide hydrolysis activity. In embodiments, the disclosure includes any one, or any combination of PEPD mutations disclosed herein, and accordingly includes the proviso that any single or any combination of such mutants can be excluded from the invention.

PEPD used in embodiments of this disclosure can include modifications that enhance its desirable characteristics, such as the capability to bind to or enter a tumor cell or tumor microenvironment, or to enhance circulation time, bioavailability, stability, or uses related to ErbB1-positive cell-targeted killing, or ErbB1-positive cell imaging. PEPD proteins that can be used with the present disclosure include a polypeptide comprising SEQ ID NO:1 or a modification thereof, and in embodiments also include such PEPD polypeptides within the context of a larger polypeptide. Modifications to SEQ ID NO:1 include modifications that abrogate or lessen enzymatic activity, and/or changes that do not affect the capability of the modified PEPD to bind to ErbB1. Thus, the PEPD of SEQ ID NO:1 can be modified by conservative amino acid substitutions that are based generally on relative similarity of R— group substituents. Non-limiting examples of such substitutions contemplated include, but are not limited to: gly or ser for ala; lys for arg; gln or his for asn; glu for asp; ser for cys; asn for gln; asp for glu; ala for gly; asn or gln for his; leu or val for ile; ile or val for leu; arg for lys; leu or tyr for met; thr for ser; tyr for trp; phe for tyr; and ile or leu for val. Thus, PEPDs that comprise any single conservative amino acid substitution, or any combination of conservative amino acid substitutions, are included in this disclosure, so long as they retain their ErbB1-binding properties, and can inhibit growth of ErbB1-positive cells. Thus, the instant disclosure includes polypeptide sequences that comprise SEQ ID NO: 1 or modifications thereof, and can include further modifications, including but not necessarily limited to additional amino acids, and/or by being provided as part a complex with other compositions of matter. Thus, the PEPD polypeptides could be part of larger proteins, such as fusion proteins, or they could be connected to other moieties. Accordingly, the PEPD proteins could be covalently or non-covalently associated with any desirable moiety that would be expected to improve their functional capabilities in accordance with the prophylaxis and/or therapy of ErbB1-positive cancers.

In general, the PEPD protein (and if desired a polypeptide sequence with which it is made as a single fusion protein) can be made using conventional techniques. For example, in embodiments, PEPD protein/fusion protein can be made using prokaryotic or eukaryotic expression systems. Thus, the disclosure provides manufacturing advantages over other ErbB1 binding partners, such as mAbs directed at ErbB1, which are expensive and time consuming to make. For recombinant production of proteins comprising or consisting of a PEPD as described herein, in general, any polynucleotide encoding the PEPD can be provided in an expression vector. "Expression vector" refers to a vector comprising protein expression control sequences operatively linked to the PEPD coding sequence. The expression vector can comprise cis-acting elements for expression, including but not limited to promoter elements, enhancer elements, origins of replication, selectable markers, transcription initiation sites, sequences that encode translation initiation sites, and any other sequence that is desirable for protein expression, depending on the expression system chosen. Suitable protein expression vectors which can be designed to express any polynucleotide sequence encoding PEPD (each of which PEPD-encoding sequences is encompassed within this disclosure) include all those known in the art, examples of which include but are not limited to cosmids, plasmids and virus-based systems that incorporate the recombinant polynucleotide encoding the PEPD. The system used to express the recombinant PEPD proteins of the invention can be any suitable organism and include but are not limited to mammalian cell expression systems, insect cell expression systems (e.g., baculovirus-based systems), yeast expression systems, plant cell expression systems, and prokaryotic expression systems. In one embodiment, E. coli is used for PEPD expression. In one embodiment, a PEPD chimeric protein is expressed recombinantly using a mammalian expression system so that the chimeric protein comprises human-specific glycosylation.

In an embodiment, a PEPD protein can be conjugated to an immunoglobulin (Ig) or a fragment thereof to provide a chimeric PEPD/Ig molecule. Such a construct is expected to be useful in involving various aspects of the immune response of the individual to facilitate targeted killing of ErbB1+ cells. The immunoglobulin or fragment thereof can be any Ig type or subtype. In this regard, previous studies have indicated that antibody-dependent cellular cytotoxicity (mediated via Fc receptor) plays an important part in trastuzumab targeting of ErbB2-positive breast cancer (Clynes et al., Nature Med, 6, 443-446, 2000; Spiridon et al., Clin Cancer Res, 10, 3542-3551, 2004). The present disclosure likewise encompasses PEPD-Fc chimeric proteins and pharmaceutical compositions comprising them. Methods for making Fc-chimeric proteins are known in the art. For example, pFUSE-Fc vectors, commercially available from InvivoGene, can be used to generate PEPD-Fc fusion hybrids. Thus, in one embodiment the disclosure includes a composition comprising a fusion protein, wherein the PEPD in a component of the fusion protein, and wherein the fusion protein comprises an Fc region of a human Ig. In various embodiments, the Fc region is an Fc region or fragments thereof is from an IgA, IgG, or IgE antibody, although Fc regions from other antibody types, or synthetic/artificial Fc regions can also be used. In embodiments, the Fc region is a human IgG2a or human IgG1 or a fragment of such Fc regions. The Fc region can comprise or consist of an amino acid sequence that is identical to an Fc region produced by a mammal, such as a human. In various embodiments, the Fc region may have between 80% to 100% (including all integers there between) amino acid sequence similarity to an Fc region produced by a mouse and/or a human. The Fc region may be an intact Fc region, meaning an entire Fc region, or may be a fragment of the Fc region. Those skilled in the art will recognize that the "Fc region" of an antibody means the "Fragment, crystallizable" region of the antibody, which comprises two heavy chains that contribute two or three constant domains (CD) depending on the class of the antibody. Nucleotide sequences encoding Fc regions, as well as the amino acid sequences of Fc regions for mouse and human immunoglobulins are well known in the art. In one embodiment, the Fc portion of the fusion proteins comprises only antibody heavy chain(s). Those skilled in the art will recognize that for demonstration of the invention using murine animal models, the Fc portion of the fusion protein may be an IgG2a or IgG2b Fc murine Ig portion, while for therapy and/or prophylaxis of disease in humans, the Fc portion is preferably an IgG1 or an IgG3 Fc portion. In certain embodiments, the Fc portion of the fusion proteins provided herein do not include antigen recognition portions (i.e., the antibody portion of the fusion proteins do not contain antibody variable regions). Thus, the fusion proteins are distinct from antibodies that do contain antigen binding portions. DNA constructs encoding the Fc-PEPD fusion proteins can be made using any conventional techniques well known to those skilled in the art. For example, the Fc-fusion encoding constructs can be made using commercially available reagents. For instance, INVIVOGEN offers the pFUSE-Fc family of plasmids developed to facilitate the construction of Fc-Fusion proteins by fusing a sequence encoding a given protein to the Fc region of an immunoglobulin (Ig). In this construct, the Fc region comprises the CH2 and CH3 domains of the IgG heavy chain and the hinge region. The hinge acts as a flexible spacer between the two parts of the Fc-fusion protein, which permits each part of the fusion protein to function independently if desired.

As described above, the disclosure includes any PEPD protein as a component of a fusion protein which can include any other amino acid sequence that would be desirable for expressing in the same open reading frame as the PEPD protein, and can include but are not limited to amino acid sequences involved in facilitating protein isolation and/or purification, for solubility, secretion, or any other function. The PEPD polypeptide can be configured N-terminal or C-terminal to the fused open reading frame, depending on the particular fusion protein to be produced. For example, the PEPD proteins can be provided with a histidine tag, such as a suitable polyhistidine tag. In embodiments, the histidine tag comprises at least six histidines in sequence. In an embodiment the his tag is a hexa-histidine peptide sequence. In an embodiment, if desired, a PEPD expression system can be configured so that the histidine tag can be removed, such as by including a tobacco etch virus (TEV)-cleavable, N-terminal hexa-histidine tag.

In non-limiting embodiments, the PEPD polypeptides can be combined with or coupled to a chemotherapeutic agent, or any other agent that has cytotoxic activity, or agents that are useful for detection and/or imaging of ErbB1-positive cells/tissues. For example, PEPD conjugates may include enzymatically active toxins and fragments thereof or small molecules. Suitable enzymatically active toxins and small molecules include docetaxel, mitoxanthrone, taxanes, diphtheria A chain, nonbinding active fragments of diphtheria toxin, exotoxin A chain (from *Pseudomonas aeruginosa*), ricin A chain, abrin A chain, modeccin A chain, alpha sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes, microtubule-targeting agents, or any anti-angiogenic agent(s).

Conjugates and combinations of the PEPD protein and chemotherapeutic agents (or other agents, such as imaging agents) may be made using any suitable techniques. In various embodiments, the PEPD protein can be produced separately from the chemotherapeutic agent, and then chemically coupled to it, or in the case of protein agents, the PEPD protein can be produced as a PEPD/protein fusion to yield a novel chimeric protein. For chemical coupling, a variety of bifunctional protein coupling agents such as N-succinimidyl-3-(2-pyriyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene) can be used to covalently join a PEPD and a chemotherapeutic or other agent, such as an imaging agent.

In another embodiment, the PEPD can be conjugated to a radioactive agent. A variety of radioactive isotopes are available for conjugating to proteins such that ErbB1-positive cells or tissues to which the PEPD bind can be imaged or selectively destroyed. For selective destruction of cells the peptides can be conjugated to a highly radioactive atom, such as At211, I131, I1125, Y90, Re186, Re188, Sm153, Bi212, P32, Pb212 and radioactive isotopes of Lu. For identifying ErbB1-positive cells, the PEPD conjugates can include a radioactive atom for scintigraphic studies, for example Tc99m (metastable technetium-99), I123, or a spin label for nuclear magnetic resonance and/or magnetic resonance imaging, such as I123, I131, In111, F19, C13, N15, O17 or Gadlinium (III) or Manganese (II). The radio-labels may be incorporated in the PEPD proteins in known ways.

The PEPD proteins can be provided in pharmaceutical compositions for administration by combining them with any suitable pharmaceutically acceptable carriers, excipients and/or stabilizers. Some suitable examples of pharmaceutically acceptable carriers, excipients and stabilizer can be found in *Remington: The Science and Practice of Pharmacy* (2005) 21st Edition, Philadelphia, Pa. Lippincott Williams & Wilkins. Further, any suitable delivery vehicle can be used in the invention, such as a controlled release delivery formulation in which the PEPD is released over a period of time. If desired, the pharmaceutical composition can comprise both PEPD and a coagulation inhibitor.

Administration of formulations comprising PEPD as described herein can be performed using any suitable route of administration, including but not limited to parenteral, intraperitoneal, intrapulmonary, oral, and intra-tumoral. Parenteral infusions include intramuscular, intravenous, intraarterial, intraperitoneal, and subcutaneous administration.

The amount of PEPD and any other active agent to be included in a composition and/or to be used in the method can be determined by those skilled in the art, given the benefit of the present disclosure. Thus, in one embodiment, an effective amount of a composition of the invention is administered. An effective amount can be an amount of the composition that inhibits growth of cells in the individual that express ErbB1, or an amount that extends the survival of the individual, or that alleviates disease symptoms associated with expression of the ErbB1 in the individual, or suppresses a malignant phenotype of cells overexpressing ErbB1.

In embodiments, the individual to whom a composition of the invention is administered has, is suspected of having, or is at risk for development and/or recurrence of any ErbB1- positive cancer. In various embodiments, the ErbB1-positive cancer can be any cancer type, including a solid tumor or a blood cancer, and/or a metastatic cancer, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, thymoma, Waldenstrom's macroglobulinemia, and heavy chain disease. In embodiments, the ErbB1 cancer is brain cancer, breast cancer, colon cancer, head and neck cancer, and lung cancer.

In embodiments, administration of a composition comprising a PEPD as disclosed herein causes cross-linking of ErbB1 monomers in cancer cells in the individual, which is followed by internalization and degradation of the ErbB1 monomers.

In certain embodiments, an individual treated according to the present disclosure will have ErbB1 positive cancer cells, and may or may not have ErbB2 positive cancer cells. Thus, in embodiments, the individual can be ErbB1+/EbrB2−, or ErbB1+/ErbB2+. In embodiments, the individual treated according to the methods of this disclosure is resistant to one or more drugs that target tyrosine kinases, or specifically target ErbB1 or ErbB2. In embodiments, the individual is resistant to at least one agent that targets an ErbB1 ligand-binding site in ErbB domain II or III, or the ErbB1 kinase domain, including but not limited to agents that bind the kinase-active conformation, or agents that bind an epitope that is only transiently exposed as ErbB1 moves from its inactive to its active state. In embodiments, the individual is resistant to at least one agent that targets ErbB1 and ErbB2. In embodiments, the individual is resistant to at least one of Cetuximab, Panitumumab, mAb 528, Gefitinib, Erlotinib, PD153035, AG1478, Trastuzumab, Pertuzumab, Lapatinib, or Afatinib.

Suitable dosages for either therapeutic or prophylactic purposes can be determined by those skilled in the art and will be based, at least in part, on consideration the individual's age, sex, size, and health, the type of delivery system used, the stage of disease, and other factors as will be apparent to the skilled artisan. In embodiments, PEPD dosing for human subjects may be similar to or the same as for cetuximab, which is typically 250-400 mg/m² weekly.

Compositions of the disclosure can be administered in conjunction with any conventional treatment regimen, including sequential or simultaneous administration of chemotherapeutic agents, passive immunotherapies, vaccines, adjuvants, the like. In particular embodiments the method can be performed in conjunction with conventional therapies that are intended to treat a disease or disorder associated with ErbB1-positive cells. For example, administration of compositions described herein can be combined with treatment modalities including but not limited to chemotherapies, surgical interventions, and radiation therapy which can be performed prior to, concurrently, or subsequent to PEPD administrations. Bearing in mind the potential for drug resistance as described above, in embodiments, the disclosure includes use of a composition comprising PEPD and another ErbB1-targeting agent, such as penitumumab, cetuximab, gefitinib, erlotinib or afatinib. In embodiments, the disclosure includes a composition comprising PEPD with the clinically used dual ErbB1/ErbB2 kinase inhibitor lapatinib. In embodiments, the disclosure includes use of compositions comprising PEPD and trastuzumab or another ErbB2-targeting agent.

In embodiments, the disclosure includes compositions and methods for using the compositions, wherein in addition to a PEPD protein, the compositions comprise an anticoagulant. In one embodiment, the anticoagulant is an agent that inhibits PEPDs degradation in vivo, so as to reduce PEPD dose required by patients. In one embodiment, the anticoagulant inhibits conversion of prothrombin to thrombin, or inhibits the participation of thrombin in clot formation. In an embodiment, the anticoagulant interferes with the clotting related function of the clot-promoting proteins known as factor X and factor II. In embodiments, the anticoagulant binds to and activates antithrombin III, and as a consequence, coagulation factors Xa and IIa are inhibited. In an embodiment, the anticoagulant is heparin, such as an unfractionated heparin preparation, or a low molecular weight form of heparin. Low molecular weight forms of heparin are known in the art (i.e., Weitz J I; Weitz, Jeffrey I. (1997). "Low-molecular-weight heparins". N Engl J Med 337 (10): 688-98). In an embodiment, the low molecular weight heparin is enoxaparin or a pharmaceutically acceptable salt thereof, such as enoxaparin sodium. In an embodiment, the inhibitor is a direct Xa inhibitor, either oral or non-oral, including but not limited to rivaroxaban, apixaban or edoxaban. In an embodiment, the anticoagulant is warfarin or coumadin. In an embodiment, the coagulation inhibitor may be an inhibitor of other blood coagulation factors, including but not limited to Factors XII, XI, IX and VII. In embodiments, the low molecular weight heparin or other anticoagulant is administered using any suitable vehicle and route of administration. In embodiments the anticoagulant is administered by subcutaneous injection. In one embodiment, the anticoagulant is administered orally. The dose of the anticoagulant can be based on the individual recipient's weight and other parameters that will be recognized by those skilled in the art given the benefit of this disclosure. In embodiments, the anticoagulant can be given prior to, concurrent with, or subsequent to the PEPD composition, and may be administered with the same number and timing of the PEPD administration(s), or may be administered according to a schedule that is different than the PEPD administration.

In another embodiment, the present disclosure provides a method for identifying whether an individual is a candidate for treatment with a composition comprising a PEPD. The method comprises obtaining a biological sample from the individual and determining whether the sample comprises ErbB1-positive cancer cells (including ErbB1 overexpressing cancer cells, relative to a control, or ErbB1 with an activating mutation), wherein determining that the biological sample comprises ErbB1-positive cancer cells is indicative that the individual is a candidate for the treatment. Thus, in embodiments, the present disclosure provides for aiding in the diagnosis, or for diagnosing an individual as in need of treatment with a composition comprising a PEPD. In embodiments, the method comprises communicating a determination of presence or absence of ErbB1-positive cancer cells in the biological sample to a health care provider so that the health care provider can, in one embodiment, recommend treatment with a composition comprising a PEPD. In embodiments, the method further comprises administering a composition comprising a PEPD to the individual.

A determination of the presence of ErbB1-positive cancer cells comprises in certain embodiments detecting in an individual or a biological sample obtained from the individual cancer cells which are positive for ErbB1 expression, or overexpress ErbB1 relative to a suitable reference, or express ErbB1 which comprises activating mutation(s). In this regard, it is considered that whether or not the tyrosine kinase activity of ErbB1 in cancer cells is ligand dependent, or is constitutively active for any reason, PEPD will remain an effective agent for inhibiting growth of cancer cells. Thus, in certain embodiments, the individual may have cancer cells that comprise ErbB that exhibits tyrosine kinase activity only in response to ligand binding, or the ErbB may exhibit constitutively active tyrosine kinase activity due to, for example, an activating mutation. Such mutations can comprise either germline ErbB1 gene mutations, or mutations that are specific in cancer cells and which may arise in response to chemotherapeutic and/or biological agents that target ErbB1, thus yielding resistance to such agents. Such ErbB1 activating mutations are known in the art. (See, for example, A F Gazdar, *Activating and resistance mutations of EGFR in non-small-cell lung cancer: role in clinical response to EGFR tyrosine kinase inhibitors* (Review) Oncogene (2009) 28, S24-S3). In general, it is considered that somatic activating ErbB1 mutations are located in the ATP-binding pocket in the receptor tyrosine kinase (TK) domain. In embodiments, activating mutations of the ErbB1 gene are found in the first four exons (18 through 21) of the TK domain. Examples include but are not necessarily limited to in-frame deletions in exon 19, which generally include amino-acid residues leucine-747 to glutamic acid-749 (ΔLRE), and account for about 44% of all ErbB1 TK mutations. A predominant single-point mutation is found in exon 21 which results in a substitution of an arginine for a leucine at codon 858 (L858R). This mutation is believed to have the highest prevalence of any single-point activating mutation in ErbB1 TK and is also believed to account for about 41% of all ErbB TK activating mutations. Overall, it is believed that deletions in exon 19 and the point mutation of L858R constitute about 90% of all ErbB1 activating mutations, and are sometimes referred to in the art as 'classical' activating mutations. Other activating mutations comprise a glycine-719 (G719) change to serine, alanine or cysteine (4% of all ErbB1 TK activating mutations). Other mutations include missense mutations which are believed to account for another 6% of ErbB1 mutations. Additional in-frame duplications and/or insertions in exon 20 are also known and are believed to account for the remaining 5% of ErbB1 TK activating mutations. Further, a variety of other activating mutations have been described with low frequency, including but not necessarily limited to V765A and T783A (<1%) in exon 20.

In an embodiment, the method of identifying whether an individual is a candidate for treatment with a composition comprising a PEPD comprises obtaining a biological sample from the individual and determining whether the sample comprises ErbB1-positive cancer cells and/or overexpresses ErbB1 by contacting the sample with a detectably labeled PEPD. Detecting a complex of ErbB1+ and detectably labeled PEPD is indicative that the individual is a candidate for treatment with a composition comprising PEPD as described herein. In an embodiment, the complex of ErbB1+ and detectably labeled PEPD is detected on a biopsy of a tumor that is suspected of comprising ErbB1-positive cells. In alternative embodiments, PEPD bound to an ErbB1-positive cell can be detected by using a detectably labeled PEPD binding partner. In embodiments, ErbB1-positive cancer cells express more ErbB than a reference. The reference can be any suitable reference, such as a matched control, a standardized value (i.e., area under a curve), and/or values for ErbB amounts expressed by a cell of the same tissue type in a sample, wherein the ErbB1 cells are not cancer cells. In general, in certain embodiments identification of a human subject as a candidate for treatment with a PEPD formulation is performed using the same or similar criteria as for identifying an individual as a candidate for therapy with other anti-ErbB agents, e.g., cetuximab or a tyrosine kinase inhibitor, which is based on clinically established parameters and will be known to the skilled artisan.

In embodiments the disclosure further provides products, e.g. articles of manufacture, which comprise PEPD pharmaceutical preparations. The products comprise isolated and/or purified PEPD. The PEPD can be an enzymatically active or inactive form of PEPD. The articles of manufacture include packaging and/or printed material. In one embodiment, the instant disclosure includes a closed or sealed package that contains a PEPD preparation. In certain embodiments, the package can comprise one or more closed or sealed vials, bottles, blister (bubble) packs, or any other suitable packaging for the sale, or distribution, or use of the PEPD pharmaceutical agents. The printed material can include printed information. The printed information can be provided on a label, or on a paper insert, or printed on the packaging material itself. The printed information can include information that identifies the PEPD agent in the package, the amounts and types of other active and/or inactive ingredients, and instructions for taking the composition, such as the number of doses to take over a given period of time, and/or information directed to a pharmacist and/or another health care provider, such as a physician, or a patient. The kit can comprise and the printed information can identify an additional agent, such as a coagulation inhibitor, that is provided separately or in combination with the PEPD agent. The printed material can include an indication that the PEPD pharmaceutical composition and/or any other agent provided with the kit is for the treatment of an ErbB1-positive cancer. The product can be provided as a kit comprising a therapeutically effective amount of a PEPD, packaged in a container, the kit further comprising a label attached to or packaged with the container, the label describing the contents of the container and providing indications and/or instructions regarding use of the contents of the container to treat ErbB1-positive cancer.

The following Examples are intended to illustrate but not limit the invention.

Example 1

This Example demonstrates that human PEPD and PEPD$^{G278D}$ each binds to the extracellular domain of human ErbB1 and cross-links two ErbB1 monomers.

Figure 1:
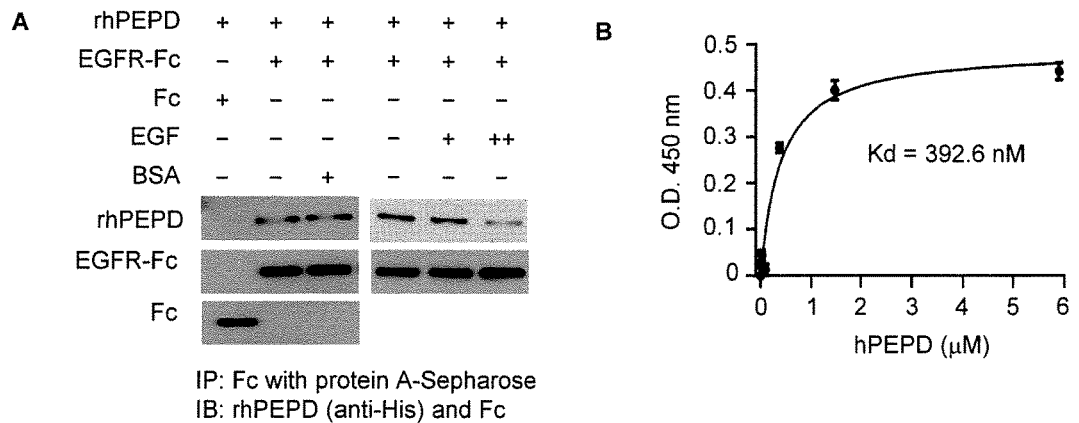
FIG. 1. Data showing that bacteria-generated recombinant human PEPD (rhPEPD) or enzymatically inactive rhPEPD$^{G278D}$ specifically binds to ErbB1 (EGFR) and cross-links two ErbB1 monomers. (A) rhPEPD (0.4 nmol/ml) was incubated with a recombinant chimera of human ErbB1 extracellular domain and the Fc fragment of human IgG1 (ErbB1-Fc) at 0.04 nmol/ml, ErbB1-Fc (0.04 nmol/ml) plus bovine serum albumin (BSA; 19 nmol/ml), or Fc (0.04 nmol/ml) for 1 h at 37° C. and then overnight at 4° C. In a separate experiment, rhPEPD (1 nmol/ml) was incubated with ErbB1-Fc (0.04 nmol/ml) in the absence or presence of epidermal growth factor (EGF; +, 5 pmol/ml; ++, 50 pmol/ml) for 1 h at 37° C. and then overnight at 4°
Figure 1:
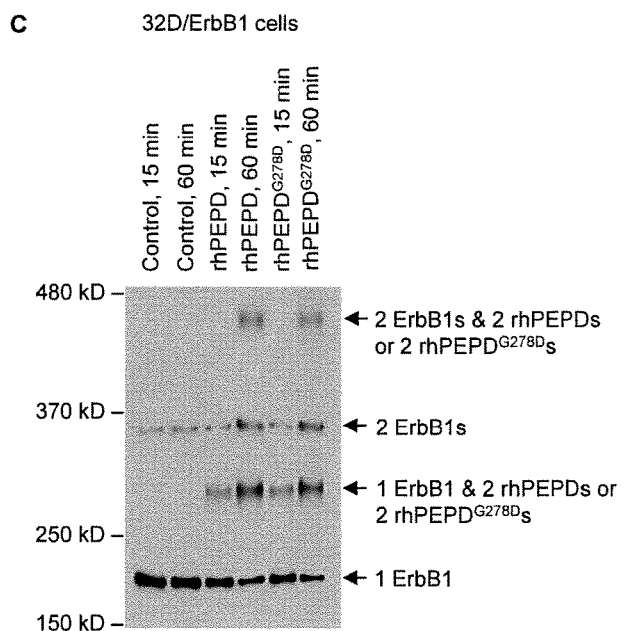

Recombinant human PEPD (rhPEPD, 0.4 nmol/ml) was incubated with a recombinant chimera of human ErbB1 extracellular domain and the Fc fragment of human IgG1 (EGFR-Fc, 0.04 nmol/ml) with or without the presence of 47.5 fold excess of bovine serum albumin (BSA; 19 nmol/ml), or incubated with the Fc (0.04 nmol/ml) of human IgG1 as a control, followed by pull-down with protein A sepharose beads and western blotting. As shown in FIG. 1A, rhPEPD bound to ErbB1 but not Fc, and the binding was not affected by BSA. rhPEPD (1 nmol/ml) was also incubated with EGFR-Fc (0.04 nmol/ml) with or without recombinant human EGF (+, 5 pmol/ml; ++, 50 pmol/ml). EGF is a high affinity ligand of EGFR/ErbB1. Whereas EGF at the low concentration did not appear to interfere with rhPEPD binding to EGFR/ErbB1, at the high concentration it significantly blocked rhPEPD binding to EGFR/ErbB1. These results show that rhPEPD binds specifically to the extracellular domain of ErbB1.

In an ELISA using the EGFR-Fc mentioned above, rhPEPD binds to it in a dose-dependent manner and in a typical receptor-ligand binding mode, with an estimated Kd value of 392.6 nM (FIG. 1B).

Murine myeloid 32D cells do not express any ErbB1 or any other ErbBs. 32D cells stably expressing human ErbB1 (32D/ErbB1) were generated by gene transfection and clone selection. 32D/ErbB1 cells were treated with vehicle, rhPEPD or rhPEPD$^{G278D}$ (5 nM), and then treated with cross-linking agent BS3 (2 mM, 30 min); cell lysates were immunoblotted for ErbB1. As shown in FIG. 1C, most ErbB1 molecules in these cells existed as monomers (monomer molecular weight of 175 kD), but some ErbB1 dimers were also detected, the latter of which likely results from ErbB1 overexpression. Both rhPEPD and rhPEPD$^{G278D}$ bind to ErbB1 as a homodimer (dimer molecular weight of 108 kD), first forming heterotrimer (1 ErbB monomer linked to 1 dimer of rhPEPD or rhPEPD$^{G278D}$) and then heterotetramer (2 ErbB1 monomers linked to 1 dimer of rhPEPD or rhPEPD$^{G278D}$) (FIG. 1C). Increased level of ErbB1 dimer free of the PEPDs was also detected, which might result from incomplete cross-linking of the proteins by BS3.

Notably, despite a Kd value of 392.6 nM as shown in FIG. 1B, both PEPD and PEPD$^{G278D}$ rapidly bind and cross-link ErbB1 at 5 nM. This suggests that the binding affinity of PEPD or PEPD$^{G278D}$ towards ErbB2 measured in vitro in a cell-free system does not fully reflect their interaction on the cell surface.

Example 2

This Example demonstrates that rhPEPD and rhPEPD$^{G278D}$ initially stimulates ErbB1 but later suppress it.

32D/ErbB1 cells, which overexpress ErbB1 but not other ErbBs, were treated with rhPEPD or rhPEPD$^{G278D}$ each at 5 nM for up to 24 h. Cells were then harvested and cell lysates were analyzed for ErbB1 level and level of phosphorylated ErbB1 (measuring phosphorylation at tyrosine 1173) by western blotting. Both agents caused ErbB phosphorylation initially, likely due to its cross-linking of ErbB monomers, but subsequently ErbB1 depletion, likely due to internalization of the ligand-bound receptor, followed by degradation.

Example 3

This Example shows that both rhPEPD and rhPEPD$^{G278D}$ disrupts ErbB1-ErbB2 heterodimer interaction.

ErbB2 is a well-known preferred heterodimerization partner for other ErbBs. In cells overexpressing both ErbB and ErbB2 (CHO-K1/ErbB1+ErbB2), with no expression of other ErbBs, rhPEPD (5 nM) caused rapid tyrosine phosphorylation of both ErbB1 and ErbB2, followed by down regulation of both ErbB1 and ErbB2, with down regulation of ErbB2 occurring much faster than that of ErbB1 (FIG. 3A). The relatively slow rate of ErbB1 down regulation, compared to that of ErbB2, may be related to a difference in their internalization and degradation.

Next, CHO-K1/ErbB1+ErbB2 cells were treated with solvent, rhPEPD or rhPEPD$^{G278D}$ (5 nM) for 1 h, with or without pretreatment with EGF (20 nM, 15 min). Cell lysates were immunoprecipitated using an ErbB2 antibody or an ErbB1 antibody, followed by immunoblotting. Even though rhPEPD and rhPEPD$^{G278D}$ bind to both ErbB1 and ErbB2, both agents disrupt ErbB1-ErbB2 association, whether the heterodimer forms spontaneously or is stimulated by EGF (FIG. 3B, 3C). Moreover, both agents caused EGF-bound ErbB1 to separate from ErbB2 (FIG. 3C).

Notably, for the immunoblots shown in FIG. 3B, sample loading was adjusted to contain an equal amount of ErbB2. An example of immunoblotting with and without ErbB2 loading adjustment is shown in FIG. 3C for comparison.

Example 4

This Example illustrates the interaction of rhPEPD or rhPEPD$^{G278D}$ with ErbB1 or ErbB2.

The PEPDs bind and cross-link ErbB1, causing dimerization, transient phosphorylation and degradation of ErbB1 (FIG. 4A). ErbB1 and ErbB2 form heterodimers with phosphorylation when overexpressed. Although the PEPDs can bind to both ErbB1 and ErbB2, they do not cross-link ErbB1 and ErbB2. Rather, the PEPDs disrupt ErbB1-ErbB2 heterodimerization by cross-linking two ErbB1 monomers and two ErbB2 monomers, leading to receptor internalization and degradation (FIG. 4B). EGF binds to ErbB1 and promotes ErbB1-ErbB2 heterodimerization, but the PEPDs disrupt such heterodimerization by binding to ErbB2 in the complex and forcing ErbB2 dimerization, internalization and degradation. However, available evidence indicates that the PEPDs may not be able to compete against EGF for binding to ErbB1.

Example 5

This Example shows that PEPD$^{G278D}$ inhibits the growth of multiple human cancer cell lines that express ErbB1, ErbB1 and ErbB2, or ErbB with an activating mutation.

The cells lines evaluated include CHO-K1 cells that stably overexpress human ErbB1 (CHO-K1 ErbB1 cells), CHO-K1 cells that stably overexpress both human ErbB1 and human ErbB2 (CHO-K1 ErbB1/ErbB2 cells), human epidermoid carcinoma A431 cells that overexpress human ErbB1, and human lung adenocarcinoma HCC827 cells that express an activating mutation in the ErbB1 tyrosine kinase domain (E746-A750 deletion). Cells were grown in 96-well plates overnight and then treated with solvent or rhPEPDG$^{278}$D for 24, 48 or 72 h, followed by measurement of cell proliferation by MTT assay. We focused on rhPEPD$^{G278D}$, as this agent is more attractive than rhPEPD as a potential therapeutic agent, as explained before. rhPEPD$^{G278D}$ inhibited the proliferation of each and every cell line in a dose-dependent manner, and cell proliferation was inhibited 85-95% after treatment with rhPEPD$^{G278D}$ at 250 nM for 72 h (FIG. 5).

Example 6

This Example shows that PEPD$^{G278D}$ does not inhibit cells that do not express ErbB1 and that PEPD$^{G278D}$ causes biphasic effect on cell proliferation (initial stimulation, followed by inhibition) in cells expressing moderate level of ErbB1.

CHO-K1 cells do not express ErbB1, ErbB3 and ErbB4, but express a minute level of ErbB2 (FIG. 7). CHO-K1 cells were treated with rhPEPD$^{G278D}$ for 72 h, but there was no inhibition of cell growth (FIG. 6B).

Hepa1c1c7 cells express a moderate level of ErbB1 and some ErbB2 (FIG. 7). These cells were treated with rhPEPD$^{G278D}$ for 24, 48 and 78 h. Cell proliferation increased up to 21.4% after 24 h treatment, but decreased up to 66.5% after 48-72 h treatment.

Example 7

This Example shows that rhPEPD$^{G278D}$ is highly effective in suppressing ErbB1 and ErbB2, regardless of cancer cell lines.

CHO-K1/ErbB1 cells, CHO-K1/ErbB1+ErbB2 cells, A431 cells and HCC827 cells all overexpress ErbB1 with significant ErbB1 phosphorylation, whereas Hepa1c1c7 cells express moderate level of ErbB1 and low ErbB1 phosphorylation, and CHO-K1 cells has no ErbB1 (FIG. 7A).

CHO-K1/ErbB+ErbB2 cells also overexpress ErbB2 with significant ErbB2 phosphorylation. HCC827 cells express a moderate level of ErbB2 with significant ErbB2 phosphorylation. CHO-K1/ErbB1 cells, A431 cells, Hepa1c1c7 cells and CHO-K1 cells show low to very low expression of ErbB2 and ErbB2 phosphorylation (FIG. 7A).

Treatment of the cells, including CHO-K1/ErbB1 cells, CHO-K1/ErbB1+ErbB2 cells, A431 cells, HCC827 cells and Hepa1c1c7 cells, with rhPEPD$^{G278D}$ at 5 and 25 nM for 24 h caused marked and dose-dependent down regulation of both ErbB1 and ErbB2 as well as loss of phosphorylated ErbB1 and ErbB2 in all cell lines examined (FIGS. 7B, 7C).

The effect of rhPEPD$^{G278D}$ on signaling molecules downstream of ErbB1 was examined in A431 cells. While rhPEPD$^{G278D}$ had no effect on the expression levels of AKT, extracellular signal-regulated kinase (ERK) or signal transducer and activator of transcription 3 (STAT3), it caused the dephosphorylation (inactivation) of all three proteins. These changes are consistent with suppression of ErbB1 as well as ErbB2 by rhPEPD$^{G278D}$.

Example 8

This Example shows that enoxaparin (EP) inhibit rhPEPD degradation in vivo and that combination of EP with rhPEPD or rhPEPD$^{G278D}$ markedly elevates plasma concentration of the latter agents.

Therapeutically relevant plasma concentrations of rhPEPD could be achieved in mice by given rhPEPD at 10 mg/kg i.p. (FIG. 8A). However, pretreatment with EP at 2.5 mg/kg i.p. allowed rhPEPD dose to be reduced by at least 50 fold without decreasing its plasma concentration (FIG. 8B). EP is a clinically used low molecular weight heparin (LMWH). EP also significantly increased plasma level of endogenous PEPD in mice (FIG. 8B). We later found that EP dose of 0.5 mg/kg daily was adequate for elevating plasma PEPD level (FIG. 8C). LMWHs including EP are known to inhibit several blood coagulation proteases, including factors Xa and IIa, via binding and activating antithrombin, a serine protease inhibitor. Our unpublished observation indicates that EP inhibits PEPD proteolysis by a novel proteolysis pathway, comprising blood coagulation proteases in the plasma, including factors XII, XI, IX, X, II and VII. Therefore, besides EP, other anticoagulants that inhibit one or more the above coagulation proteases may also block the degradation of rhPEPD and rhPEPD$^{G278D}$ in vivo.

Example 9

This Example shows that both rhPEPD and rhPEPD$^{G278D}$ inhibit tumor growth in mice, but rhPEPD$^{G278D}$ shows a more favorable outcome.

We evaluated the antitumor activity of the PEPDs using the orthotopic BT-474 breast cancer model. Human breast cancer BT-474 cells were inoculated to the mammary fat pads of female athymic mice. Treatment was started after tumor size reached approximately 230 mm$^3$. The mice were treated with vehicle, EP, EP plus rhPEPD or EP plus rhPEPD$^{G278D}$. EP was administered to the mice i.p. at 0.5 mg/kg daily, started 4 days before rhPEPD or rhPEPD$^{G278D}$ rhPEPD or rhPEPD$^{G278D}$ was administered to the mice i.p. at 2 mg/kg twice, separated by 2 days. The mice were killed 24 h after the final dose of each treatment, and tumors and blood samples were obtained at that time. After treatment with only two doses of rhPEPD or rhPEPD$^{G278D}$, the tumors shrank to 42.2% or 37.3% of control, respectively (FIG. 9A). EP impacted neither tumor growth nor ErbB signaling in the tumor tissues, while tumor inhibition by the PEPDs was associated with marked depletion and dephosphorylation of ErbB2 and ErbB1, and dephosphorylation (inactivation) of key downstream signals, including SRC, AKT, extracellular signal-regulated kinase (ERK) and signal transducer and activator of transcription 3 (STAT3) (FIG. 9B). Low levels of ErbB3 were also present in BT-474 tumors; both agents reduced ErbB3 tyrosine phosphorylation but not its expression (FIG. 9B), which is consistent with our finding that the PEPDs are not ligands of ErbB3 but disrupt heterodimerization of ErbB1 or ErbB2. While SRC is activated upon binding to activated ErbB1 or ErbB2, phosphoinositide 3-kinase (PI3K) activation and signaling in ErbB1- or ErbB2-overexpressing cancer cells depend on its recruitment to activated ErbB3 in the ErbB heterodimers. Accordingly, both agents strongly inhibited SRC kinase activity and PI3K activity in the tumor tissues (FIGS. 9C, 9D). Each agent also downregulated anti-apoptotic B-cell lymphoma 2 (Bcl-2), up regulated pro-apoptotic Bcl-2-associated X protein (BAX) and activated caspases-3/-8/-9 in the tumor tissues (FIG. 9B). However, rhPEPD, but not rhPEPD$^{G278D}$, stimulated hypoxia-inducible factor 1α (HIF-1α) and its downstream targets, including vascular endothelial growth factor (VEGF) and glucose transporter 1 (GLUT-1) in the tumor tissues. The effects of rhPEPD or HIF-1a, VEGF and GLUT-1 likely stem from the metabolism of imidodipeptides by rhPEPD upon its internalization and the inhibition of HIF-1a degradation by the metabolites (Surazynski et al., International Journal of Cancer, 122, 1435-1440, 2008). Both rhPEPD and rhPEPD$^{G278D}$ accumulated in the tumor tissues.

Example 10

This Example shows that rhPEPD$^{G278D}$ strongly inhibits ErbB1-overexpressing tumors in vivo.

We further evaluated the antitumor activity of rhPEPD$^{G278D}$ in a mouse subcutaneous model of head and neck cancer which overexpresses ErbB1. Human A341 cancer cells were inoculated subcutaneously to the flank of male athymic mice (2.7×10$^6$ cells per site). The mice were then randomized to three experimental groups: no treatment, EP, and EP plus rhPEPD$^{G278D}$. EP treatment (0.5 mg/kg i.p.

daily) was started when tumor volume reached approximately 40 mm³. Five days later, tumor volume reached approximately 100 mm³, and the EP-treated mice also began treatment with either solvent or rhPEPD$^{G278D}$ (4 mg/kg) every other day. Some of the EP-treated mice were treated with rhPEPD$^{G278D}$ (4 mg/kg, every other day for a total of two doses) when tumor size reached approximately 450 mm³.

High plasma concentrations of rhPEPD$^{G278D}$ were reached in mice treated with rhPEPD$^{G278D}$ at 4 mg/kg in combination with EP (FIG. 10A).

As shown in FIG. 10B, while EP has no effect on tumor growth, rhPEPD$^{G278D}$ is highly effective in inhibiting tumor growth. When the tumor was relatively small (approximately 100 mm³), rhPEPD$^{G278D}$ totally stopped tumor growth after the first dose, and when the tumor was relatively large (approximately 450 mm³), rhPEPD$^{G278D}$ caused profound tumor regression after the first dose. Moreover, while EP had no effect on ErbB1 and other signaling molecules in the tumor tissues, rhPEPD$^{G278D}$ down regulated both ErbB1 and ErbB2, caused dephosphorylation (inactivation) of both ErbB1 and ErbB2, and dephosphorylation of AKT, ERK and STAT3 in the tumor tissues (FIG. 10C). The molecular changes in the tumor tissues induced by rhPEPD$^{G278D}$ are identical to that in cultured A431 cells (FIG. 7C).

The mice showed no sign of toxicity, and neither EP nor rhPEPD$^{G278D}$ had any effect on body weight gain (FIG. 10D).

Example 11

This Example provides a description of the materials and methods that were used to obtain the data described in the Examples 1-10.

Reagents. rhPEPD and rhPEPD$^{G278D}$ (6×His tagged to the carboxy terminus) were generated as previously described (Yang et al., Journal of Biological Chemistry, 288, 2365-2375, 2013). Recombinant Fc of human IgG$_1$, recombinant EGFR-Fc (a chimera of the extracellular domain (Met$^1$-Ser$^{45}$) of human EGFR and the Fc fragment of human IgG$_1$), and recombinant EGF were from R&D Systems. EP and methylthiazolyldiphenyl tetrazolium bromide (MTT) were purchased from Sanofi-Aventis and Sigma-Aldrich, respectively.

The following antibodies were used: anti-PEPD (Abcam), anti-human IgG$_1$ for detection of Fc (Santa Cruz), anti-EGF (R&D Systems), anti-ErbB1 (Cell Signaling), anti-p-ErbB1 (Y1173) (Cell Signaling), anti-ErbB2 (Cell Signaling), anti-p-ErbB2 (Y1221/1222) (Cell Signaling), anti-AKT (Cell Signaling), anti-ErbB3 (Santa Cruz), anti-p-AKT (Cell Signaling), anti-ERK (Cell Signaling), anti-p-ERK (Cell Signaling), anti-SRC (Cell Signaling), anti-p-SRC (Cell Signaling), anti-STAT3 (Cell Signaling), anti-p-STAT3 (Cell Signaling), anti-caspase-3 (Cell Signaling), anti-cleaved caspase-8 (Cell Signaling), anti-cleaved caspase-9 (Cell Signaling), anti-Bcl-2 (Cell Signaling), anti-Bax (Cell Signaling), anti-VEGF (Santa Cruz), anti-GLUT-1 (Santa Cruz), anti-HIF-1a (Santa Cruz), anti-GAPDH (Millipore), biotin-conjugated anti-His (Bethyl), HRP-conjugated streptavidin (Thermo Scientific), and a goat anti-rabbit IgG-HRP (Jackson ImmunoResearch).

Cell Lines, Cell Culture, and Gene Transfection.

32D cells with stable expression of wild-type human EGFR/ErbB1 (32D/ErbB1) were provided by Gibbes R Johnson at the US Food and Drug Administration. 32D/ErbB1 cells were cultured in RPMI1640 medium supplemented with 10% fetal bovine serum (FBS), 5% WEHI-3B cell-conditioned medium, and 0.1% 2-mercaptoethanol. Human breast cancer MCF-7 cells (ATCC) were cultured in high-glucose DMEM plus 10% FBS. BT-474 cells (ATCC) were cultured in 50% high-glucose DMEM/50% F-12K medium plus 10% FBS. CHO-K1 cells (ATCC) as well as CHO-K1 subclones that overexpress ErbB1, ErbB2, or ErbB plus ErbB2, as described below, were cultured in F-12K medium plus 10% FBS. HCC827 cells (ATCC) were cultured in RPMI-1640 medium plus 10% FBS. A-431 cells were cultured in 50% DMEM/50% F-12K medium plus 10% FBS. All cell lines were cultured in humidified incubators at 37° C. with 5% CO$_2$.

CHO-K1/ErbB2 cells, which stably overexpress human ErbB2, were generated by transfecting CHO-K1 cells with pcDNA-ERBB2 and selected under G418. To transiently overexpress human ErbB1, CHO-K1 cells or CHO-K1/ErbB2 cells were transfected with pCMV6-XL5-ERBB1. Transient gene transfection was carried out using cells grown in 6-well plates and FuGENE HD (Promega).

Western Blot Analysis.

Cells were harvested from culture by trypsin treatment and centrifugation. After washing twice with PBS, cells were lysed in 1× cell lysis buffer (Cell Signaling) supplemented with 2 mM phenylmethanesulfonyl fluoride and a proteinase inhibitor cocktail (Roche Applied Science). Cell lysis was enhanced by sonication. The samples were cleared by centrifugation at 13,000×g for 10 min at 4° C. Tumor tissues were mixed with RIPA buffer (25 mM Tris-HCl, pH 7.6, 150 mM NaCl, 1% NP-40, 1% sodium deoxycholate, 0.1% SDS) supplemented with the proteinase inhibitor cocktail from Roche and stroked in a Dounce homogenizer, and the homogenate was cleared by centrifugation at 13,000×g for 15 min at 4° C. Protein concentrations of all specimens were measured by the BCA assay kit (Pierce). The samples were mixed with 4× loading dye, heated for 5 min at 95° C. and resolved by SDS-PAGE (8-10%). The proteins were transferred to polyvinylidene fluoride membrane and probed with specific antibodies, and protein bands were detected using the ECL Plus kit (Amersham) or the SuperSignal West Pico kit (Thermo Scientific).

To detect binding of rhPEPD or rhPEPD$^{G278D}$ to ErbB1 in live cells, cells were treated with each agent or solvent, followed by wash with ice-cold PBS or incubation with cross linker BS3 (Pierce) at 2 mM for 30 min at room temperature. The cross-linking reaction was terminated by adding 50 mM Tris (final, pH 7.5), followed by incubation at room temperature for 15 min. Cell lysates were analyzed by western blotting (3.5% SDS-PAGE).

Immunoprecipitation.

For detection of direct and specific binding of rhPEPD to ErbB1, rhPEPD (0.4 μM) was incubated in M-PER buffer with EGFR-Fc (0.04 μM) or Fc (0.04 μM) with or without BSA (19 μM) or EGF (5 or 50 nM) for 1 h at 37° C. and then overnight at 4° C., followed by incubation with protein A-sepharose for 1 h at room temperature. The beads were washed with immunoprecipitation washing buffer and subjected to western blot analysis. In experiments using cell lysates, cells were lysed in M-PER Buffer (Thermo Scientific) supplemented with a proteinase inhibitor mix (Roche Applied Science). Cell lysates (0.5 mg of total protein in 0.5 ml binding buffer) were incubated with an antibody overnight at 4° C. The immunocomplexes were pulled down by protein G-agarose (1 h incubation at room temperature). The beads were washed with IP washing buffer and then subjected to western blot analysis.

ELISA for Measurement of Plasma PEPD Concentration and for PEPD Binding Affinity Towards ErbB1.

To measure PEPD concentration, 96-well ELISA plates were coated with 100 µl/well of diluted an anti-PEPD mouse monoclonal antibody (2.5 µg/ml) at 4° C. overnight. The plates were then washed three times with phosphate buffered saline with Tween 20 (PBST) and blocked with 200 µl/well of blocking buffer (incubation for at least 2 h at room temperature). The plates were washed with PBST and then incubated with 100 µl/well of PEPD standard or samples, which were appropriately diluted, for 2 h at room temperature. The plates were washed three times with PBST, and each well was then incubated with 100 µl of a detection antibody (an anti-PEPD rabbit polyclonal antibody) for 2 h at room temperature. After washing the plates three times with PBST, 100 µl of secondary reagent (goat-anti-rabbit IgG-HRP, 1:2500 dilution) were added to each well, followed by 1 h incubation at room temperature. The plates were washed again with PBST three times, and each well was then incubated with 100 µl of a HRP substrate solution (TMB substrate from Cell Signaling, #7004). After adequate color development, 100 µl of stop solution (Cell Signaling, #7002) was added to each well, and absorbance at 450 nm was recorded by a microtiter plate reader. Pure PEPD was used as a standard.

To measure PEPD or EGF binding to EGFR, 96-well ELISA plates were coated overnight at 4° C. with 100 µl/well of goat-anti-human IgG Fc (10 µg/ml). After washing three times with PBST, residual protein binding sites in the wells were saturated by incubating for 2 h at room temperature with 300 µl/well of assay buffer (1% BSA/PBS). After removing the assay buffer, 60 µl of rhPEPD were added to each well, followed by addition of 60 µl of EGFR-Fc (1 g/ml) to each rhPEPD-containing well and incubation at 37° C. for 2 h. The plates were then washed three times with PBST, and 100 µl of biotin-conjugated goat-anti-His (1:10000 dilution) were added to each well and incubated for 2 h at room temperature. After another round of washing with PBST, 100 µl of streptavidin-conjugated HRP (1:10000 dilution) was added to each well and incubated for 45 min at room temperature. The wells were washed again with PBST, and the bound HRP was detected by addition of 100 µl/well of TMB solution as a peroxidase substrate. The reaction was terminated by addition of 100 µl/well of stop solution, and absorbance reading at 450 nm was recorded by a microtiter plate reader.

PI3 Kinase Assay.

A PI3-Kinase Activity ELISA Kit (Echelon, K-1000s) was used. Briefly, PI3K was pulled down from whole cell lysates (prepared from approximately $1 \times 10^6$ cells per sample) using an PI3K antibody (anti-PI3K p85), and the immunoprecipitates were mixed with 30 µl of KBZ reaction buffer, which was then mixed with 30 µl of 10 µM PI(4,5)P$_2$ substrate, followed by incubation for 2 h at 37° C. The kinase reaction was terminated by adding 90 µl of kinase stop solution to each reaction solution, and 60 µl of each stopped kinase reaction solution was transferred together with 60 µl of PIP$_3$ detector to each well in the incubation plate. After incubation at room temperature for 60 min, 100 µl per sample from the incubation plate was transferred to the corresponding wells of the detection plate and incubated for 60 min at room temperature. The plates were washed with TBST and then incubated with the HRP-conjugated secondary detector for 30 min, followed by washing with TBST, and the immobilized HRP was measured by a standard colorimetric assay, using 3,3',5,5'-tetramethylbenzedine as a substrate.

Src Kinase Assay.

Src activity in cell lysates was measured using the Universal Tyrosine Kinase Assay Kit (TaKaRa, #MK410). Briefly, lysates (prepared from approximately $1 \times 10^6$ cells per sample) were pre-cleared with protein A-agarose beads prior to IP with a Src antibody. The immunoprecipitates were washed and incubated with 10 mM β-mercaptoethanol in 150 µl of kinase reaction solution. Each sample (40 µl) was mixed with 10 µl of 40 mM ATP-2Na solution, which was transferred to microtiter plate wells coated with a PTK substrate, followed by incubation at 37° C. for 30 min. After wash with TBST, an HRP-conjugated anti-phosphotyrosine (PY20) solution was added to each well and incubated for 30 min at 37° C. After another round of wash with TBST, the immobilized HRP was measured by a standard colorimetric assay, using 3,3',5,5'-tetramethylbenzedine as a substrate.

MTT Cell Proliferation Assay.

Cells were growth in 96-well plates (150 µl medium per well) overnight and then treated with vehicle or rhPEPD$^{G278D}$ for up to 72 h, followed by incubation with MTT (9.2 mM in medium) for 3 h at 37° C. After removing the medium, the cells were treated with dimethyl sulfoxide (150 µl per well), and formazan formed from MTT (which is proportional to cell density) was measured spectroscopically at 570 nm.

Animal Study.

Athymic mice (Harlan Laboratories) were used for the studies. All animal experiments were performed in accordance with protocols approved by the Institutional Animal Care and Use Committee at Roswell Park Cancer Institute. rhPEPD was evaluated in an orthotopic mammary tumor model, whereas rhPEPD$^{G278D}$ was evaluated in both the orthotopic mammary tumor model and a subcutaneous epidermal adenocarcinoma model.

To establish orthotopic mammary tumors, we implanted female athymic mice (6-7 weeks of age) with 1.7 mg 60-day release 17β-estradiol pellets (Innovative Research of America) subcutaneously and 2 days later inoculated BT-474 cells to the mammary fat pads at $2 \times 10^6$ per site in 100 µl of PBS-Matrigel mixture (1:1). Tumors were allowed to reach approximately 230 mm$^3$. The mice were then treated with vehicle, EP, EP plus rhPEPD, EP plus rhPEPD$^{G278D}$. We gave EP (0.5 mg/kg) i.p. once daily for 7 days, and on the fifth and seventh days of EP treatment, we also gave rhPEPD or rhPEPD$^{G278D}$ i.p. at 2 mg/kg. The mice were killed 24 h after the final treatment. On the days when both EP and rhPEPD or rhPEPD$^{G278D}$ were given, EP was always given 1 h earlier than the other agent. EP, rhPEPD and rhPEPD$^{G278D}$ were given in PBS (100 µl/20 g body weight). We calculated tumor size using length×width$^2$/2. Tumor images were captured using a Canon EOS Digital Rebel Xsi camera.

To establish subcutaneous A431 tumors, we inoculated A431 cells to the flank of male athymic mice (5 weeks of age) subcutaneously at $2.7 \times 10^6$ cells in 100 µl of serum-free medium per site. The mice were randomized into three groups: no treatment, EP, or EP plus rhPEPD$^{G278D}$. EP treatment (0.5 mg/kg i.p. daily) was initiated when tumor volume reached approximately 40 mm$^3$. Five days later, when tumor volume reached approximately 100 mm$^3$, while EP treatment continued, the mice were also treated with either vehicle or rhPEPD$^{G278D}$ (4 mg/kg) every other day. Some of the EP-treated mice were treated with rhPEPD$^{G278D}$ (4 mg/kg, every other day for a total of two doses) when tumor size reached approximately 450 mm$^3$. On the days when both EP and rhPEPD$^{G278D}$ were given to mice, EP was always given 1 h earlier than the other agent. EP and rhPEPD$^{G278D}$ were given in PBS (100 µl/20 g body weight). Blood samples as well as tumors were obtained from the mice at 24 h after the last treatment or at the same time from the untreated mice. Plasma concentrations of endogenous mouse PEPD and/or rhPEPD$^{G278D}$ were determined by ELISA.

Statistical Analysis.

ANOVA was used for multi-group comparison. P value of 0.05 or lower was considered statistically significant.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A method for prophylaxis or therapy of ErbB1-positive cancer in an individual comprising administering to the individual an effective amount of a composition comprising peptidase D (PEPD), the PEPD comprising the sequence of SEQ ID NO:1 with a mutation of G278, such that growth of the ErbB1-positive cancer is inhibited.

2. The method of claim 1, further comprising administering an anticoagulant to the individual.

3. The method of claim 1, wherein the PEPD is a component of a fusion protein.

4. The method of claim 2, wherein the PEPD is a component of a fusion protein.

5. The method of claim 1, wherein the mutation of G278 is G278D.

* * * * *